United States Patent
Warrellow et al.

(10) Patent No.: US 6,465,471 B1
(45) Date of Patent: Oct. 15, 2002

(54) CINNAMIC ACID DERIVATIVES

(75) Inventors: Graham John Warrellow, Northwood; John Clifford Head, Maidenhead; John Robert Porter, Chinnor; Sarah Catherine Archibald, Maidenhead, all of (GB)

(73) Assignee: Celltech Therapeutics Limited (GB)

( * ) Notice: Subject to any disclaimer, the term of this patent is extended or adjusted under 35 U.S.C. 154(b) by 0 days.

(21) Appl. No.: 09/346,235

(22) Filed: Jul. 1, 1999

(30) Foreign Application Priority Data

Jul. 3, 1998 (GB) .............................. 9814414

(51) Int. Cl.$^7$ .................. A61K 31/4406; C07D 213/55
(52) U.S. Cl. ................ 514/256; 514/332; 514/336; 514/342; 514/354; 514/355; 514/356; 514/357; 514/423; 514/427; 544/335; 546/262; 546/269.7; 546/313; 546/316; 546/323; 546/337; 548/537; 548/560; 548/561
(58) Field of Search .............................. 546/269.7, 316, 546/323, 262, 313, 337; 514/332, 336, 354, 355, 356, 342, 357, 256, 423, 427; 548/537, 560, 561; 544/335

(56) References Cited

U.S. PATENT DOCUMENTS

| | | | | |
|---|---|---|---|---|
| 4,470,973 A | 9/1984 | Natarajan et al. | ............ | 424/177 |
| 4,554,273 A | 11/1985 | Bayssat et al. | ............ | 514/221 |
| 4,987,132 A | 1/1991 | Mase et al. | ................. | 514/252 |
| 5,164,372 A | 11/1992 | Matsuo et al. | ................. | 514/19 |
| 5,167,693 A | * 12/1992 | Drewes et al. | ................. | 71/92 |
| 5,227,490 A | 7/1993 | Hartman et al. | ............ | 514/317 |
| 5,296,486 A | 3/1994 | Lazer et al. | ................ | 514/333 |
| 5,399,585 A | 3/1995 | Alig et al. | .................. | 514/438 |
| 5,510,346 A | 4/1996 | Martin et al. | ............... | 514/221 |
| 5,698,691 A | 12/1997 | Yukimasa et al. | .......... | 540/490 |
| 5,703,106 A | * 12/1997 | Fruh et al. | .................. | 514/378 |
| 5,773,646 A | 6/1998 | Michael et al. | ............. | 562/439 |
| 5,977,075 A | * 11/1999 | Ksander et al. | ............... | 514/19 |
| 6,093,696 A | 7/2000 | Head et al. | ................... | 514/19 |

FOREIGN PATENT DOCUMENTS

| | | |
|---|---|---|
| DE | 23 16 881 A | 10/1973 |
| DE | 28 37 264 A1 | 3/1979 |
| DE | 196 54 483 A | 1/1998 |
| EP | 0 031 104 A1 | 7/1981 |
| EP | 0 048 763 A1 | 4/1982 |
| EP | 0 144 230 A | 6/1985 |
| EP | 0 288 176 A | 10/1988 |
| EP | 0 322 068 A1 | 6/1989 |
| EP | 0 394 989 A2 | 10/1990 |
| EP | 0 498 268 A2 | 8/1992 |
| EP | 0 596 406 A1 | 5/1994 |
| EP | 0 710 657 A1 | 5/1996 |
| EP | 0 710 659 A1 | 5/1996 |
| EP | 0 842 943 A2 | 5/1998 |
| EP | 0 842 945 A2 | 5/1998 |
| JP | 56 090045 | 7/1981 |
| JP | 03 135962 | 6/1991 |
| WO | WO 86/02353 | 4/1986 |
| WO | WO 93/00095 | 1/1993 |
| WO | WO 93/08174 | 4/1993 |
| WO | WO 93/09795 | 5/1993 |
| WO | WO 94/15954 | 7/1994 |
| WO | WO 94/15955 | 7/1994 |
| WO | WO 94/29285 | 12/1994 |
| WO | WO 95/13811 | 5/1995 |
| WO | WO 95/15973 | 6/1995 |
| WO | WO 95/19356 | 7/1995 |
| WO | WO 95/35314 | 12/1995 |
| WO | WO 96/01644 | 1/1996 |
| WO | WO 96/22966 | 8/1996 |
| WO | WO 96/26190 | 8/1996 |
| WO | WO 97/03094 | 1/1997 |
| WO | WO 97/08145 | 3/1997 |
| WO | WO 97/12866 | 4/1997 |
| WO | WO 97/23480 | 7/1997 |
| WO | WO 97/24124 | 7/1997 |
| WO | WO 97/31907 | 9/1997 |
| WO | WO 97/36858 | 10/1997 |
| WO | WO 97/36859 | 10/1997 |
| WO | WO 97/36861 | 10/1997 |
| WO | WO 97/36862 | 10/1997 |
| WO | WO 97/44333 | 11/1997 |
| WO | WO 97/47618 | 12/1997 |
| WO | WO 98/00395 | 1/1998 |
| WO | WO 98/04247 | 2/1998 |
| WO | WO 98/04913 | 2/1998 |
| WO | WO 98/18460 | 5/1998 |
| WO | WO 98/25892 | 6/1998 |
| WO | WO 98/31359 | 7/1998 |
| WO | WO98/42662 | 10/1998 |
| WO | WO 98/53814 | 12/1998 |

(List continued on next page.)

OTHER PUBLICATIONS

Fruh et al., Chemical Abstracts, vol. 124:146859, 1995.*
Ksander et al., Chemical Abstracts, vol. 131:322919, 1999.*

(List continued on next page.)

Primary Examiner—Richard Raymond
(74) Attorney, Agent, or Firm—Woodcock Washburn LLP

(57) ABSTRACT

Compounds of formula (1) are described:

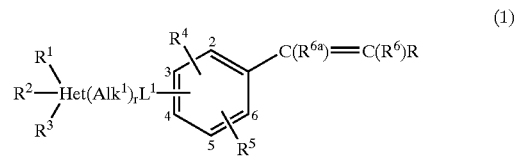

(1)

in which Het is a heteroaromatic group, $Alk^1$ is an optionally substituted aliphatic or heteroaliphatic chain and R is a carboxylic acid or a derivative thereof. The compounds are able to inhibit the binding of $\alpha_4$ integrins to their ligands and are of use in the prophylaxis and treatment of immune or inflammatory disorders.

19 Claims, No Drawings

FOREIGN PATENT DOCUMENTS

| | | |
|---|---|---|
| WO | WO 98/53817 | 12/1998 |
| WO | WO 98/53818 | 12/1998 |
| WO | WO 98/54207 | 12/1998 |
| WO | WO 98/58902 | 12/1998 |
| WO | WO 99/06390 | 2/1999 |
| WO | WO 99/06431 | 2/1999 |
| WO | WO 99/06432 | 2/1999 |
| WO | WO 99/06433 | 2/1999 |
| WO | WO 99/06434 | 2/1999 |
| WO | WO 99/06435 | 2/1999 |
| WO | WO 99/06436 | 2/1999 |
| WO | WO 99/06437 | 2/1999 |
| WO | WO 99/10312 | 3/1999 |
| WO | WO 99/10313 | 3/1999 |
| WO | WO 99/20272 | 4/1999 |
| WO | WO 99/26921 | 6/1999 |
| WO | WO 99/26922 | 6/1999 |
| WO | WO 99/26945 | 6/1999 |
| WO | WO 99/30709 | 6/1999 |
| WO | WO 99/31061 | 6/1999 |
| WO | WO 99/31099 | 6/1999 |
| WO | WO 99/32457 | 7/1999 |
| WO | WO 99/35163 | 7/1999 |
| WO | WO 99/36393 | 7/1999 |
| WO | WO 99/37618 | 7/1999 |
| WO | WO 99/43642 | 9/1999 |
| WO | WO 99/44994 | 9/1999 |
| WO | WO 99/48879 | 9/1999 |
| WO | WO 99/52879 | 10/1999 |
| WO | WO 99/52896 | 10/1999 |
| WO | WO 99/52898 | 10/1999 |
| WO | WO 99/60015 | 11/1999 |
| WO | WO 99/61465 | 12/1999 |
| WO | WO 99/64395 | 12/1999 |
| WO | WO 99/67230 | 12/1999 |
| WO | WO 00/00486 | 1/2000 |
| WO | WO 00/01383 | 1/2000 |
| WO | WO 00/06169 | 2/2000 |
| WO | WO 00/07544 | 2/2000 |
| WO | WO 00/17197 | 3/2000 |
| WO | WO 00/20396 | 4/2000 |
| WO | WO 00/23419 | 4/2000 |
| WO | WO 00/31067 | 6/2000 |
| WO | WO 00/35855 | 6/2000 |
| WO | WO 00/73260 | 12/2000 |

OTHER PUBLICATIONS

Drewes et al., Chemical Abstracts, vol. 116:151783, 1992.*
Denny et al., Chemical Abstracts, vol. 129:67696, 1998.*
Oku et al., Chemical Abstracts, vol. 128:13212, 1997.*
Heitsch et al., Chemical Abstracrs, vol. 128:30416, 1997.*
Oku et al., Chemical Abstracts, vol. 127:220659, 1997.*
Oku et al., Chemical Abstracts, vol. 125:142578, 1996.*
Fujisawa et al., Chemical Abstracts, vol. 124:202256, 1996.*
Oku et al., Chemical Abstracts, vol. 123:28507, 1995.*
Konishi et al., Chemical Abstracts, vol. 122:105641, 1995.*
Oku et al., Chemical Abstracts, vol. 122:105897, 1995.*
Muenster et al., Chemical Abstracts, vol. 117:7793, 1992.*
Saito et al., Chemical Abstracts, vol. 116:106269, 1992.*
Hammadi, A., et al., "Diastereoselective hydrogenation of monodehydro enkephalins controlled by chiral rhodium catalysts," *Tetrahedron: Asymmetry*, 1992, 3(10), XP002106601, 1247–1262.
Nunami, K., et al., "A novel synthesis of methyl 1,5–disubstituted imidazole–4–carboxylates using 3–bromo–2–isocyanoacrylates," *J. Org. Chem.*, 1994, 59, XP002106602, 7635–7642.

Shimohigashi, Y., et al., "Dehydro–enkephalins," *Int. J. Peptide Protein Res.*, 1983, 21, XP002106600, 202–208.
Strange, P.G., et al., "Studies of enzyme–mediated reactions. Part II. Stereochemistry of the elimination of ammonia form L–tyrosine catalysed by the enzyme from maize," *J. Chem. Soc., Perkin I*, 1972, 18, XP002106603, 2364–2372.
WPI/Derwent No. XP002106604, Japanese Patent No. JP 60 190749 (Mitsui Toatsu Chem. Inc.), Sep. 28, 1985, 1 page, Abstract only.
Rico, J.G. et al., "A highly stereoselective michael addition to an $\alpha$, $\beta$–unsaturated ester as the crucial step in the synthesis of a novel $\beta$–amino acid–containing fibrinogen receptor antagonist", *J. Org. Chem*, 1993, vol. 58, pp. 7948–7951.
Zablocki, J.A. et al., "Potent in vitro and in vivo inhibitors of platelet aggregation based upon the Arg–Gly–Asp sequences of fibrinogen", *J. Med. Chem.*, 1995, vol. 38, pp. 2378–2394.
Alhaique, F., et al., "Cyclisation of dinitriles by sodium alkoxides a new synthesis of naphthyridines," *Tetrahedron Letters*, 1975, 3, 173–174.
Ames, D.E., et al., "Condensation of $\beta$–dicarbonyl compounds with halogenopyridinecarb–oxylic acids. A convenient synthesis of some naphthyridine derivatives," *J.C.S. Perkin I*, 1972, 705–710.
Bodor, N., "Novel approaches in prodrug design," *Alfred Benzon Symposium*, 1982, 17, 156–177.
Brooks, Peter C., et al., "Antiintegrin $\alpha v \beta 3$ blocks human breast cancer growth and angiogenesis in human skin," *J. Clin. Invest.*, 1995, 96, 1815–1822.
Bundgaard, H., *Design of Prodrugs*, 1985, Elsevier, Amsterdam.
Katritzky, A.R., et al. (Eds.), Comprehensive Organic Functional Group Transformations, Pergamon, 1995.
Davies, S..G., et al., "Asymmetric synthesis of R–$\beta$–amino butanoic acid and S–$\beta$–tyrosine: homochiral lithium amide equivalents for Michael additions to $\alpha,\beta$–unsaturated esters," *Tetra. Asymmetry*, 1991, 2(3), 183–186.
Erle, D.J., et al., "Expression and function of the Mad-CAM–1 receptor, integrin $\alpha 4\beta 7$, on human leukocytes," *J. Immunol.*, 1994, 153, 517–528.
Encyclopedia of Reagents for Organic Synthesis, *John Wiley and Sons (eds.)*, 1995.
Giacomello, et al., "Synthesis of 2,6–naphthyridine," *Tetra. Letters*, 1965, 16, 1117–1121.
Green, T.W., et al., "Protective Groups in Organic Synthesis," *John Wiley and Sons (eds.)*, 1991.*
Hammadi, A., et al., "Diastereoselective hydrogenation of monodehydro enkephalins controlled by chiral rhodium catalysts," *Tetrahedron: Asymmetry*, 1992, 3(10), XP002106601, 1247–1262.*
Hammes, H., et al., "Subcutaneous injection of a cyclic peptide antagonist of vitronectin receptor–type integrins inhibits retinal neovascularization," *Nature Medicine*, 1996, 2, 529–533.*
Hodivala–Dilke, K.M., "$\beta 3$–integrin–deficient mice are a model for glanzmann thrombasthenia showing placental defects and reduced survival," *J. Clin. Invest.*, 1999, 103(2), 229–238.*
Kalvin, D.M., et al., Synthesis of (4R)–D,L–[4–$^2$H]– and (4S)–D,L–[4–$^2$H] homoserine lactones, *J. Org. Chem.*, 1985, 50, 2259–2263.*
Koivunen, E., et al., "Selection of peptides binding to the $\alpha_5\beta_1$ integrin from phage display library," *J. Biological Chemistry*, 1993, 268(27), 20205–20210.*

Mitjans, F., et al., "An anti–αv–integrin antibody that blocks integrin function inhibits the development of a human melanoma in nude mice," *J. Cell Science*, 1995, 108, 2825–2838.*

Molina, P., et al., "Iminophosphorane–mediated annelation of a pyridine ring into a preformed pyridine one: synthesis of naphthyridine, pyrido [1,2–c] pyrimidine and pyrido [1,2–c] quinazoline derivatives," *Tetrahedron*, 1992, 48(22), 4601–4616.*

Newham, P., et al., "Integrin adhesion receptors: structure, function and implications for biomedicine," *Nolecular Medicine Today*, 1996, 304–313.*

Numata, A., et al., "General synthetic method for naphthyridines and their N–oxides containing isoquinolinic nitrogen," *Synthesis*, 1999, 2, 306–311.*

Nunami, K., et al., "A novel synthesis of methyl 1,5–disubstituted imidazole–4–carboxylates using 3–bromo–2–isocyanoacrylates," *J. Org. Chem.*, 1994, 59, XP002106602, 7635–7642.*

Sakamoto, T., et al., "Condensed heteroaromatic ring systems. III. synthesis of naphthyridine derivatives by cyclization of ethynylpyridinecarboxamides," *Chem. Pharm. Bull.* 1985, 33(2), 626–633.

Shimohigashi, Y., et al., "Dehydro–enkephalins," *Int. J. Peptide Protein Res.*, 1983, 21, XP002106600, 202–208.

Singh, G., et al., "Prodrug approach in new drug design and development," *J. Sci. Ind. Res.*, 1996, 55, 497–510.

Srivatsa, S.S., et al., "Selective αvβ3 integrin blockade potently limits neointimal hyperplasia and lumen stenosis following deep coronary arterial stent injury: evidence for the functional importance of integrin αvβ3 and osteopontin expression during neointima formation," *Cariovascular Research*, 1997, 36, 408–428.

Strange, P.G., et al., "Studies of enzyme–mediated reactions. Part II. Stereochemistry of the elimination of ammonia form L–tyrosine catalysed by the enzyme from maize," *J. Chem. Soc., Perkin I*, 1972, 18, XP002106603, 2364–2372.

Stupack, D.G., et al., "induction of $\alpha_v\Theta_3$ integrin–mediated attachment to extracellular matrix in $\beta_1$ integrin (CD29)–negative B cell lines," *Experi, Cell Research*, 1992, 203, 443–448.

Tan R., et al., "Synthesis of 2, 6–naphthyridine and some of its derivatives," *Tetrahedron Letters*, 1965, 31, 2737–2744.

WPI/Derwent No. XP002106604, Japanese Patent No. JP 60 190749 (Mitsui Toatsu Chem. Inc.), Sep. 28, 1985, 1 page, Abstract only.

Abraham, W.M. et al., "$\alpha_4$–Integrins Mediate Antigen–Induced Late Bronchial Responses and Prolonged Airway Hyperresponsiveness in Sheep", *J. Clin. Invest.*, 1994, 93, 776–787.

Berlin, C. et al., "α4β7 Integrin Mediates Lymphocyte Binding to the Mucosal Vascular Addressin MAdCAM–1", *Cell*, 1993, 74, 185–195.

Binns, R.M. et al., "The Role of E–Selectin in Lymphocyte and Polymorphonuclear Cell Recruitment into Cutaneous Delayed Hypersensitivity Reactions in Sensitized Pigs", *J. Immunol.*, 1996, 157, 4094–4099.

Briskin, M.J. et al., "Structural Requirements for Mucosal Vascular Addressin Binding to Its Lymphocyte Receptor $\alpha_4\beta_7$", *J. Immunol.*, 1996, 156, 719–726.

Cardarelli, P.M. et al., "Cyclic RGD Peptide Inhibits α4β7 Interaction with Connecting Segment 1 and Vascular Cell Adhesion Molecule", *J. Biol. Chem.*, 1994, 269(28), 18668–18673.

Corey, E.J. et al., "A Synthetic Method for Formyl → Ethynyl Conversion (RCHO → RC ≡CH or RC ≡CR')", *Tetrahedron Lett.*, 1972, 36, 3769–3772.

Ferguson, T.A. et al., "Two integrin–binding peptides abrogate T cell–mediated immune responses in vivo", *Proc. Natl. Acad. Sci. USA*, 1991, 88, 8072–8076.

Holzmann, B. et al., "Peyer's patch–specific lymphocyte homing receptors consist of a VLA–4–like α chain associated with either of two integrin β chains, one of which is novel", *EMBO J.*, 1989, 8(6), 1725–1741.

Humphries, M.J. et al., "Mechanisms of VCAM–1 and fibronectin binding to integrin $\alpha_4\beta_1$: implications for integrin function and rational drug design", *Ciba Foundation Symposium*, 1995, 189, 177–194.

Issekutz, T.B., "Inhibition of Lymphocyte Endothelial Adhesion and In Vivo Lymphocyte Migration to Cutaneous Inflammation by TA–3, a New Monoclonal Antibody to Rat LFA–1", *J. Immunol.*, 1992, 149(10), 3394–3402.

Lei, H. et al., "Efficient Synthesis of a Phosphinate Bis–Amino Acid and Its Use in the Construction of Amphiphilic Peptides", *J. Org. Chem.*, 1994, 59, 4206–4210.

Li, Z. et al., "Effect of an anti–Mo1 MAb on ozone–induced airway inflammation and airway hyperresponsiveness in dogs", *Am. J. Physiol.*, 1992, 263(6 Pt 1), L723–726.

Marlin, S.D. et al., "LFA–1 Immunodeficiency Disease", *J. Exp. Med.*, 1986, 164, 855–867.

Nagasawa, H.T. et al., "β–Substituted Cysteines as Sequestering Agents for Ethanol–Derived Acetaldehyde in Vivo", *J. Med. Chem.*, 1987, 30, 1373–1378.

Osborne, L., "Leukoctye Adhesion to Endothelium in Inflammation", *Cell*, 1990, 62, 3–6.

Osborn, L. et al., "Direct Expression Cloning of Vascular Cell Adhesion Molecule 1, a Cytokine–Induced Endothelial Protein that Binds to Lymphocytes", *Cell*, 1989, 59, 1203–1211.

Podolsky, D.K. et al., "Attenuation of Colitis in the Cotton–top Tamarin by Anti–α4 integrin Monoclonal Antibody", *J. Clin. Invest.*, 1993, 92, 372–380.

Shroff, H.N. et al., "Small Peptide Inhibitors of $\alpha_4\beta_7$ Mediated MAdCAM–1 Adhesion to Lymphocytes", *Barge. Med. Chem. Letts.*, 1996, 6(21), 2495–2500.

Sonnenberg, A., "Interins and Their Ligands", *Curr. Topics Microbiol. Immunol.*, 1993, 184, 7–35.

Springer, T.A., "Adhesion receptors of the immune system", *Nature*, 1990, 346, 425–434.

Springer, T.A., "Traffic Signals for Lymphocyte Recirculation and Leukocyte Emigration: The Multistep Paradigm", *Cell*, 1994, 76, 301–314.

Vanderslice, P. et al., "A Cyclic Hexapeptide is a Potent Antagonist of α4 Integrins", *J. Immunol.*, 1997, 158, 1710–1718.

Yang, X., "A predominant role of integrin α4 in the spontaneous development of autoimmune diabetes in nonobese diabetic mice", *Proc. Natl. Acad. Sci. USA*, 1994, 91, 12604–12608.

Yednock, T.A., "Prevention of experimental autoimmune encephalomyelitis by antibodies against α4β1 integrin", *Nature*, 1992, 356, 63–66.

WPI / Derwent No. XP–002076854, Japanese Patent No. JP 04 193 895 A (Ajinomoto, K.K.), Jul. 13, 1992, DW9234, 1 Page, Abstract Only.

WPI / Derwent No. XP–002076855, Japanese Paent No. JP 56 049 373 A (Dainippon Pharm Co Ltd), May 2, 1981, DW8125, 1 Page, Abstract Only.

Bach et al., "Anomalous optical rotation and circular dichroism of N–thioacylated.alpha.–amino acids and deriva," *Acta Chem. Scand.*, 1966, 20(10), 2781–2794.

Barrett, G.C., "Circular dichroism of N–thiobenzoly–1–α–amino acids. III. Their circular dichroism through the near–ultraviolet wavelength range," *J. Chem. Soc.*, 1967, Section C, 1–5.

*Chemical Abstracts*, "N–[4–Thiazolidinyl)carbonyl]amino acid derivatives," 1981, 95(19), Abstract No. 169173f, 1 page.

Cornforth, J.W., "Oxazoles and Oxazolones," *Chem. Penicillin*, Princeton Book Review, 1949, pp. 688, 799, and 800.

Fu, H. et al., "Preliminary study on synthesis and antitumor activity in vitro of derivatives of timonacic," *Chemicals Abstracts*, 1988, 108(17), Abstract No. 150358k, 1 page.

Harris, R.L.N. et al., *Aust. J. Chem.*, "Potential wool growth inhibitors. 2(1H)–Pyridone analogs of mimosine," 1977, 30(3), 649–655.

Hartke, K. et al., "Dithio and thiono esters. Part 61. Synthesis of α–amino dithioesters and endothiodipeptides,", *J. Prakt. Chem.*, 1996, 338(3), 251–256.

Jaynes, B.H. et al., "Synthesis and In Vivo Antibacterial Activity of Hygromycin a Analogs Modified at the $C_4$' Aryl Position," *Bioorg. Med. Chem. Letts.*, 1993, 3(8), 1531–1536.

Jepson, J.B. et al., "Reactions of α–Thioacylamino–acids. Their conversion into Thiazolones and Derivatives Thereof," *J. Chem. Soc.*, 1955, 1791–1797.

Masahiko, N., Japanese Patent No. 57–080370 published May 19, 1982, "Alpha–Methylcinnamic Acid Derivative, its Preparation and Antilipemic Agent Containing The Same," *Patent Abstracts of Japan*, 1982, 1 page.

Noike, Y., "Synthesis of Quinolizine Derivatives. VI. Synthesis of 3–Aminoquinolizines. (1). Synthesis of dl–3–Amino–, dl–3–epi–Amino–, and dl–3–epi–Dimethylaminoquinolizidines," *Yakugaku Zasshi*, 1959, 79(12), 1514–1518 (English summary included).

Ohki, S. et al., "Synthesis of quinolizine derivatives. V. Studies on Diastereoisomer of Ethyl 3–Quinolizidinecarboxylate," *Chem. Pharm. Bull.*, 1959, 7(6), 708–712.

Schultz, Von O.–E. et al., "Analogs of nuleic acid based as antimetabolites," *Arzneimittel Forschung. Drug. Res.*, 1967, 17(8), 1060–1064 (English summary included).

Tsunematsu, H. et al., "Hydrolysis of phenylthiazolones of p–guanidinophenylalanine and arginie by trypsin and related enzymes," *J. Biochem.*, 1983, 94(4), 1119–1125.

Whitlock, B.J. et al., "Structure and synthesis of lathyrine," *J. Org. Chem.*, 1965, 30, 115–118.

Yanagisawa, H. et al., WO 97/37970, "Preparation of phenylalkylcarboxylic acid derivatives lowering blood sugar level," *Chemical Abstracts*, 1997, Abstract 127:307307, 4 pages.

Azzouny, A.E., et al., "Synthesis of some N–substituted salicylamides structurally related to certain antimicrobials," *Pharmazie*, 1977, 32(6), 318–323 (abstract).

Badshah, A., et al., "Catalytic reduction of azlactones in alkaline media. Synthesis of amino acids," *J. of Organic Chemistry*, 1972, 37(18), 2916–2918.

Tous, G., et al., "O'–(Epoxyalkyl) tyrosines and (Epoxyalkyl) phenylalanine as irreversible inactivators of serine proteases: synthesis and inhibition mechanism," *J. of Medicinal Chemistry*, 1990, 33(6), 1620–1634.

Clausen, K., et al., "Studies on amino acids and peptides. II. Synthesis of protected endothiodipeptides," *J. Chem. Scr.*, 1982, 20(1–2), 14–18, doc. No. 97:163474 (abstract only, 1 page).

Frank, R., et al., "Extremely mild reagent for Boc deprotection," *J. Chem. Commun. (Cambridge)*, 1996, 22, 2509–2510, doc. No. 126:104395 (abstract only, 3 pages).

Kobayashi, A., et al., "Syntheses of 2–dialkylamino–4, 4–disubstituted 5 (4H)–thiazolones," *J. Yakugaku Zasshi*, 1970, 90(11), 1377–1380, doc. No. 74:31713 (abstract only, 3 pages).

Koenig, H.B., et al., ".beta.–Lactam antibiotics," *Ger. Offen.*, 41 pages, doc. No. 83:97276 (abstract only, 5 pages) 1975.

Masuda, T., *Jpn. Kodai Tokkyo Koho*, 22 pages, doc. No. 115:280022 (abstract only, 1 page) 1996.

Pfeifer, T., et al., "Specific fragmentation of thioxo peptides facilitates the assignment of the thioxylated amino acid," *J. Mass Spectrom*, 1997, 32(10), 1064–1071, doc. No. 127:331738 (abstract only 2 pages).

Sawa, N., et al., "Preparation of 4(5)–thiocarbamoylimidazole compounds," *Jpn. Kokai Tokkyo Koho*, 33 pages, doc. No. 115:183296 (abstract only, 2 pages), 1991.

Schutkowski, M., et al., "Inhibition of peptidyl–prolyl cis/trans isomerase activity by substrate analog structures: thioxo tetrapeptide–4–nitroanilides," *Biochemistry*, 1995, 34(40), 13016–13026, doc. No. 123:221511 (abstract only, 4 pages).

"Cephalosporins," *Jpn. Kokai Tokkyo Koho*, 40 pages, doc. No. 99:5433 (abstract only, 2 pages), 1983.

Lobb, R.R., et al., "Small molecule antagonists of alpha4 integrins: novel drugs for asthma," *Exp. Opin, Invest. Drugs*, 1999, XP000885957, 8(7), 935–945.

Samanen, J., et al., "Vascular indications for integrin alpha V antagonists," *Current Pharm. Design.*, 1997, 3, 545–584.

Šavrda, J., "CIS–TRANS isomerism of N–ACYL derivatives of proline and its analogues, linear peptides with CIS peptide bonds," *Proc. 14th European Peptide Symposium*, Loffet, A. (ed.), 1976, 653–656.

Buckle, D.R., et al., "Non Thiazolidinedione Antihyperglycaemic Agents. 1: α–Heteroatom Substituted β–Phenylpropanoic Acids," *Bioorg. Med. Chem. Lett.*, 1996, 6(17), 2121–2126.

Keenan, R.M. et al., "Discovery of Potent Nonpeptide Vitronectin Receptor ($av\beta_3$) Antagonists, " *J. Med. Chem.*, 1997, 40(15), 2289–2292.

McDowell, R.S. et al., "From Peptide to Non–Peptide. 2. The *de Novo* Design of Potent, Non–Peptidal Inhibitors of Platelet Aggregation Based on a Benzodiazepinedione Scaffold", *J. Am. Chem. Soc.*, 1994, 116, 5077–5083.

Miller, W.H. et al., "Structure–Activity Relationships in 3–Oxo–1, 4–Benzodiazepine–2–Acetic Acid GPIIb/IIIa Antagonists. The 2–Benzazepine Series," *Bioorg. Med. Chem. Lett.*, 1996, 6(21), 2481–2486.

Ukai, Y. et al., "A novel synthetic inhibitor of endopeptidase–24.15," *Chemical Abstracts*, 1997, 127(2), 1 page.

Venturella, V.S. et al., "Substituted 1,3–Dihydro–4H–furo [3,4–d]–1, 3–benzodiazepin–3–ones: Synthesis and Scope of the Method," *J. Heterocyclic Chem.*, 1969, 6(5), 671–679.

Wojciechowska, H. et al., "Preparation of 2,4–dinitrophenyl derivatives of tyrosine," *Chemical Abstracts, 1968, 68(25)*, Abstract No. 114926r, 1 page.

* cited by examiner

CINNAMIC ACID DERIVATIVES

This invention relates to a series of cinnamic acid derivatives, to compositions containing them, to processes for their preparation, and to their use in medicine.

Over the last few years it has become increasingly clear that the physical interaction of inflammatory leukocytes with each other and other cells of the body plays an important role in regulating immune and inflammatory responses [Springer, T A. Nature, 346 425, (1990); Springer, T. A. Cell 76, 301, (1994)]. Many of these interactions are mediated by specific cell surface molecules collectively referred to as cell adhesion molecules.

The adhesion molecules have been sub-divided into different groups on the basis of their structure. One family of adhesion molecules which is believed to play a particularly important role in regulating immune and inflammatory responses is the integrin family. This family of cell surface glycoproteins has a typical non-covalently linked heterodimer structure. At least 14 different integrin alpha chains and 8 different integrin beta chains have been identified [Sonnenberg, A. Current Topics in Microbiology and Immunology, 184, 7, (1993)]. The members of the family are typically named according to their heterodimer composition although trivial nomenclature is widespread in this field. Thus the integrin termed α4β1 consists of the integrin alpha 4 chain associated with the integrin beta 1 chain, but is also widely referred to as Very Late Antigen 4 or VLA4. Not all of the potential pairings of integrin alpha and beta chains have yet been observed in nature and the integrin family has been subdivided into a number of subgroups based on the pairings that have been recognised [Sonnenberg, A. ibid].

The importance of cell adhesion molecules in human leukocyte function has been further highlighted by a genetic deficiency disease called Leukocyte Adhesion Deficiency (LAD) in which one of the families of leukocyte integrins is not expressed [Marlin, S. D. et al J. Exp. Med. 164, 855 (1986)]. Patients with this disease have a reduced ability to recruit leukocytes to inflammatory sites and suffer recurrent infections which in extreme cases may be fatal.

The potential to modify adhesion molecule function in such a way as to beneficially modulate immune and inflammatory responses has been extensively investigated in animal models using specific monoclonal antibodies that block various functions of these molecules [e.g. Issekutz, T. B. J. Immunol. 3394, (1992); Li, Z. et al Am. J. Physiol. 263, L723, (1992); Binns, R. M. et al J. Immunol. 157, 4094, (1996)]. A number of monoclonal antibodies which block adhesion molecule function are currently being investigated for their therapeutic potential in human disease.

One particular integrin subgroup of interest involves the α4 chain which can pair with two different beta chains β1 and β7 [Sonnenberg, A. ibid]. The α4β1 pairing occurs on many circulating leukocytes (for example lymphocytes, monocytes and eosinophils) although it is absent or only present at low levels on circulating neutrophils. α4β1 binds to an adhesion molecule (Vascular Cell Adhesion Molecule-1 also known as VCAM-1) frequently up-regulated on endothelial cells at sites of inflammation [Osborne, L. Cell, 62, 3, (1990)]. The molecule has also been shown to bind to at least three sites in the matrix molecule fibronectin [Humphries, M. J. et al. Ciba Foundation Symposium, 189, 177, (1995)]. Based on data obtained with monoclonal antibodies in animal models it is believed that the interaction between α4β1 and ligands on other cells and the extracellular matrix plays an important role in leukocyte migration and activation [Yednock, T. A. et al, Nature, 356, 63, (1992); Podolsky, D. K. et al. J. Clin. Invest. 92, 373, (1993); Abraham, W. M. et al. J. Clin. Invest. 93, 776, (1994)].

The integrin generated by the pairing of α4 and β7 has been termed LPAM-1 [Holzmann, B and Weissman, I. EMBO J. 8, 1735, (1989)] and like α4β1, binds to VCAM-1 and fibronectin. In addition, α4β7 binds to an adhesion molecule believed to be involved in the homing of leukocytes to mucosal tissue termed MAdCAM-1 [Berlin, C. et al, Cell, 74, 185, (1993)]. The interaction between α4β7 and MAdCAM-1 may also be important at sites of inflammation outside of mucosal tissue [Yang, X-D. et al, PNAS, 91, 12604 (1994)].

Regions of the peptide sequence recognised by α4β1 and α4β7 when they bind to their ligands have been identified. α4β1 seems to recognise LDV, IDA or REDV peptide sequences in fibronectin and a QIDSP sequence in VCAM-1 [Humphries, M. J. et al, ibid] whilst α4β7 recognises a LDT sequence in MAdCAM-1 [Briskin, M. J. et al, J. Immunol. 156, 719, (1996)]. There have been several reports of inhibitors of these interactions being designed from modifications of these short peptide sequences [Cardarelli, P. M. et al J. Biol. Chem. 269, 18668, (1994); Shroff, H. N. Bioorganic. Med. Chem. Lett. 6, 2495, (1996); Vanderslice, P. J. Immunol. 158, 1710, (1997)]. It has also been reported that a short peptide sequence derived from the α4β1 binding site in fibronectin can inhibit a contact hypersensitivity reaction in a trinitrochlorobenzene sensitised mouse [Ferguson, T. A. et al, PNAS 88, 8072, (1991)].

Since the alpha 4 subgroup of integrins are predominantly expressed on leukocytes their inhibition can be expected to be beneficial in a number of immune or inflammatory disease states. However, because of the ubiquitous distribution and wide range of functions performed by other members of the integrin family it is very important to be able to identify selective inhibitors of the alpha 4 subgroup.

We have now found a group of compounds which are potent and selective inhibitors of α4 integrins. Members of the group are able to inhibit α4 integrins such as α4β1 and/or α4β7 at concentrations at which they generally have no or minimal inhibitory action on a integrins of other subgroups. The compounds are thus of use in medicine, for example in the prophylaxis and treatment of immune or inflammatory disorders as described hereinafter.

Thus according to one aspect of the invention we provide a compound of formula (1)

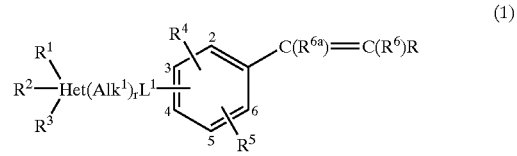

wherein

Het is a heteroaromatic group;

$R^1$, $R^2$ and $R^3$ which may be the same or different is each an atom or group —$L^2(Alk^2)_tL^3(R^7)_u$ in which $L^2$ and $L^3$ which may be the same or different is each a covalent bond or a linker atom or group, t is zero or the integer 1, u is an integer 1, 2 or 3, $Alk^2$ is an aliphatic or heteroaliphatic chain and $R^7$ is a hydrogen or halogen atom or a group selected from alkyl, —$OR^8$ [where $R^8$ is a hydrogen atom or an optionally substituted alkyl group], —$SR^8$, —$NR^8R^9$ [where $R^9$ is as just defined for $R^8$ and may be the same or different], —$NO_2$, —CN, —CO$_2$R$^8$, —OCO$_2$R$^8$, —CONR$^8$R$^9$, —OCONR$^8$R$^9$, —CSNR$^8$R$^9$, —COR$^8$, —OCOR$^8$, —N(R$^8$)COR$^9$, —N(R$^8$)CSR$^9$, —SO$_2$N(R$^8$)(R$^9$), —N(R$^8$)SO$_2$R$^9$, —N(R$^8$)CON(R$^9$)(R$^{10}$), [where R$^{10}$ is a hydrogen atom or an optionally substituted alkyl group] —N(R$^8$)CSN(R$^9$)(R$^{10}$) or —N(R$^8$)SO$_2$N(R$^9$)(R$^{10}$);

Alk$^1$ is an optionally substituted aliphatic or heteroaliphatic chain;

L$^1$ is a covalent bond or a linker atom or group;

R$^4$ and R$^5$, which may be the same or different, is each a hydrogen or halogen atom or an alkyl, alkoxy, hydroxy or nitro group;

R$^6$ and R$^{6a}$, which may be the same or different, is each an atom or group —L$^2$(Alk$^2$)$_t$L$^3$R$^{11}$ in which L$^2$, L$^3$, Alk$^2$ and t are as previously defined and R$^{11}$ is a hydrogen or halogen atom or an —OR$^8$, —NR$^8$R$^9$, —NO$_2$, —CN, —CO$_2$R$^8$, —CONR$^8$R$^9$, —COR$^8$, —N(R$^8$)COR$^9$, —N(R$^8$)CSR$^9$, —SO$_2$N(R$^8$)(R$^9$), —N(R$^8$)SO$_2$R$^8$, —N(R$^8$)CON(R$^9$)(R$^{10}$), —N(R$^8$)CSN(R$^9$)(R$^{10}$), —N(R$^8$)SO$_2$N(R$^9$)(R$^{10}$), or an optionally substituted aliphatic, heteroaliphatic, cycloaliphatic, heterocycloaliphatic, aromatic or heteroaromatic group;

r is zero or the integer 1;

R is a carboxylic acid (—CO$_2$H) or a derivative thereof; and the salts, solvates, hydrates and N-oxides thereof.

It will be appreciated that compounds of formula (1) exist as geometric isomers (E or Z isomers). The compounds may also have one or more chiral centres, and exist as enantiomers or diastereomers. The invention is to be understood to extend to all such geometric isomers, enantiomers, diasteromers and mixtures thereof, including racemates. Formula (1) and the formulae hereinafter are intended to represent all individual isomers and mixtures thereof, unless stated or shown otherwise.

In the compounds of formula (1), derivatives of the carboxylic acid group R include carboxylic acid esters and amides. Particular esters and amides include —CO$_2$Alk$^5$ and —CONR$^8$R$^9$ groups as described herein.

In general, the substituents R$^1$, R$^2$ and R$^3$ in compounds of the invention may be positioned on any available carbon atom, or, when present, nitrogen atom in the heteroaromatic group represented by Het.

When in the compounds of formula (1) L$^1$, L$^2$ and/or L$^3$ is present as a linker atom or group it may be any divalent linking atom or group. Particular examples include —O— or —S— atoms or —C(O)—, —C(O)O—, —C(S)—, —S(O)—, —S(O)$_2$—, —N(R$^{12}$)— [where R$^{12}$ is a hydrogen atom or an optionally substituted alkyl group], —CON(R$^{12}$), —OC(O)N(R$^{12}$), —CSN(R$^{12}$)—, —N(R$^{12}$)CO—, —N(R$^{12}$)C(O)O—, —N(R$^{12}$)CS—, —S(O)$_2$N(R$^{12}$)—, —N(R$^{12}$)S(O)$_2$—, —N(R$^{12}$)CON(R$^{12}$)—, —N(R$^{12}$)CSN(R$^{12}$), or —N(R$^{12}$)SO$_2$N(R$^{12}$)— groups. Where the linker group contains two R$^{12}$ substituents, these may be the same or different.

When R$^4$, R$^5$, R$^7$, R$^8$, R$^9$, R$^{10}$ and/or R$^{12}$ in the compounds of formula (1) is an alkyl group it may be a straight or branched C$_{1-6}$alkyl group, e.g. a C$_{1-3}$alkyl group such as a methyl or ethyl group. Optional substituents which may be present on such groups include for example one, two or three substituents which may be the same or different selected from halogen atoms, for example fluorine, chlorine, bromine or iodine atoms, or hydroxy or C$_{1-6}$alkoxy e.g. methoxy or ethoxy groups.

Alkoxy groups represented by R$^4$ and/or R$^5$ in compounds of formula (1) include C$_{1-6}$alkoxy groups such as methoxy or ethoxy groups. Halogen atoms represented by R$^4$ and/or R$^5$ include fluorine, chlorine, bromine, or iodine atoms.

When Alk$^1$ in compounds of formula (1) is an optionally substituted aliphatic chain it may be an optionally substituted C$_{1-10}$ aliphatic chain. Particular examples include optionally substituted straight or branched chain C$_{1-6}$ alkyl, C$_{2-6}$ alkenyl, or C$_{2-6}$ alkynyl chains.

Heteroaliphatic chains represented by Alk$^1$ include the aliphatic chains just described but with each chain additionally containing one, two, three or four heteroatoms or heteroatom-containing groups. Particular heteroatoms or groups include atoms or groups L$^4$ where L$^4$ is as defined above for L$^1$ when L$^1$ is a linker atom or group. Each L$^4$ atom or group may interrupt the aliphatic chain, or may be positioned at its terminal carbon atom to connect the chain to an adjoining atom or group.

Particular examples of aliphatic chains represented by Alk$^1$ include optionally substituted —CH$_2$—, —CH$_2$CH$_2$—, —CH(CH$_3$)—, —C(CH$_3$)$_2$—, —(CH$_2$)$_2$CH$_2$—, —CH(CH$_3$)CH$_2$—, —(CH$_2$)$_3$CH$_2$—, —CH(CH$_3$)CH$_2$CH$_2$—, —CH$_2$CH(CH$_3$)CH$_2$—, —C(CH$_3$)$_2$CH$_2$—, —(CH$_2$)$_4$CH$_2$—, —(CH$_2$)$_5$CH$_2$—, —CHCH—, —CHCHCH$_2$—, —CH$_2$CHCH—, —CHCHCH$_2$CH$_2$—, —CH$_2$CHCHCH$_2$—, —(CH$_2$)$_2$CHCH—, —CC—, —CCCH$_2$—, —CH$_2$CC—, —CCCH$_2$CH$_2$—, —CH$_2$CCCH$_2$—, or —(CH$_2$)$_2$CC— chains. Where appropriate each of said chains may be optionally interrupted by one or two atoms and/or groups L$^4$ to form an optionally substituted heteroaliphatic chain. Particular examples include optionally substituted —L$^4$CH$_2$—, —CH$_2$L$^4$CH$_2$—, —L$^4$(CH$_2$)$_2$—, —CH$_2$L$^4$(CH$_2$)$_2$—, —(CH$_2$)$_2$L$^4$CH$_2$—, —L$^4$(CH$_2$)$_3$— and —(CH$_2$)$_2$L$^4$(CH$_2$)$_2$— chains. The substituents which may be present on aliphatic or heteroaliphatic chains represented by Alk$^1$ include one, two, three or more substituents where each substituent may be the same or different and is selected from halogen atoms, e.g. fluorine, chlorine, bromine or iodine atoms, or C$_{1-6}$alkoxy, e.g. methoxy or ethoxy, thiol, C$_{1-6}$alkylthio e.g. methylthio or ethylthio, amino or substituted amino groups. Substituted amino groups include —NHR$^{13}$ and —N(R$^{13}$)$_2$ groups where R$^{13}$ is an optionally substituted straight or branched alkyl group as defined above for R$^{12}$. Where two R$^{13}$ groups are present these may be the same or different.

Particular examples of substituted chains represented by Alk$^1$ include those specific chains just described substituted by one, two, or three halogen atoms such as fluorine atoms, for example chains of the type —CH(CF$_3$)—, —C(CF$_3$)$_2$—, —CH$_2$CH(CF$_3$)—, —CH$_2$C(CF$_3$)$_2$—, —CH(CF$_3$)— and —C(CF$_3$)$_2$CH$_2$.

When Alk$^2$ is present in the compounds of formulae (1) or (1a) as an aliphatic or heteroaliphatic chain it may be for example any of the above-mentioned C$_{1-10}$aliphatic or heteroaliphatic chains described for Alk$^1$.

Halogen atoms represented by R$^7$ and/or R$^{11}$ include fluorine, chlorine, bromine, or iodine atoms.

When R$^{11}$ is present in compounds of formula (1) as an optionally substituted aliphatic or heteroaliphatic group it may be an aliphatic or heteroaliphatic group equivalent to the aliphatic or heteroaliphatic chain just described for Alk$^1$. Each aliphatic or heteroaliphatic group may be optionally substituted by one, two, three or more substituents where each substituent may be the same or different and is selected from halogen atoms, e.g. fluorine, chlorine, bromine or iodine atoms, or hydroxyl, C$_{1-6}$alkoxy, e.g. methoxy or ethoxy, thiol, C$_{1-6}$alkylthio e.g. methylthio or ethylthio, —NH$_2$ or substituted amino such as —NHR$^{13}$ or —N(R$^{13}$)$_2$ as described above.

Optionally substituted cycloaliphatic groups represented by $R^{11}$ include optionally substituted $C_{3-10}$ cycloaliphatic groups. Particular examples include optionally substituted $C_{3-10}$cycloalkyl, e.g. $C_{3-7}$cycloalkyl or $C_{3-10}$ cycloalkenyl e.g. $C_{3-7}$cycloalkenyl groups.

Optionally substituted heterocycloaliphatic groups represented by $R^{11}$ include the optionally substituted cycloaliphatic groups just described for $R^{11}$ but with each group additionally containing one, two, three or four heteroatoms or heteroatom-containing groups $L^4$ where $L^4$ is as defined above.

Particular examples of $R^{11}$ cycloaliphatic and heterocycloaliphatic groups include optionally substituted cyclopropyl, cyclobutyl, cyclopentyl, cyclohexyl, cycloheptyl, 2-cyclobuten-1-yl, 2-cyclopenten-1-yl, 3-cyclopenten-1-yl, tetrahydrofuranyl, pyrroline, e.g. 2- or 3-pyrrolinyl, pyrrolidinyl, pyrrolidinone, oxazolidinyl, oxazolidinone, dioxolanyl, e.g. 1,3-dioxolanyl, imidazolinyl, e.g. 2-imidazolinyl, imidazolidinyl, pyrazolinyl, e.g. 2-pyrazolinyl, pyrazolidinyl, thiazolinyl, thiazolidinyl, pyranyl, e.g. 2- or 4-pyranyl, piperidinyl, piperidinone, 1,4-dioxanyl, morpholinyl, morpholinone, 1,4-dithianyl, thiomorpholinyl, piperazinyl, 1,3,5-trithianyl, oxazinyl, e.g. 2H-1,3-, 6H-1,3-, 6H-1,2-, 2H-1,2- or 4H-1,4-oxazinyl, isoxazinyl, oxathiazinyl, e.g. 1,2,5 or 1,2,6-oxathiazinyl, or 1,3,5-oxadiazinyl groups.

The optional substituents which may be present on the $R^{11}$ cycloaliphatic, or heterocycloaliphatic groups include one, two, three or more substituents each represented by $R^{14}$ in which $R^{14}$ is a halogen atom, e.g. a fluorine, chlorine, bromine or iodine atom, or a $C_{1-6}$alkoxy, e.g. methoxy or ethoxy, thiol, $C_{1-6}$alkylthio e.g. methylthio or ethylthio amino or substituted amino group, e.g. a —$NHR^{13}$ or —$N(R^{13})_2$ group as described above. Additionally, when $R^{11}$ is a heterocycloaliphatic group containing one or more nitrogen atoms each nitrogen atom may be optionally substituted by a group —$(L^5)_p(Alk^3)_qR^{15}$ in which $L^5$ is —C(O)—, —C(O)O—, —C(S)—, —S(O)$_2$—, —CON$(R^{12})$—, —CSN$(R^{12})$—, —SON$(R^{12})$— or SO$_2$N$(R^{12})$—; p is zero or an integer 1; Alk$^3$ is an optionally substituted aliphatic or heteroaliphatic chain; q is zero or an integer 1; and $R^{15}$ is a hydrogen atom or an optionally substituted cycloaliphatic, heterocycloaliphatic, polycycloaliphatic, polyheterocycloaliphatic, aromatic or heteroaromatic group.

Optionally substituted aliphatic or heteroaliphatic chains represented by Alk$^3$ include those chains described above for Alk$^1$.

Optionally substituted cycloaliphatic or heterocycloaliphatic groups represented by $R^{15}$ include those groups just described for $R^{11}$. Optional substituents which may be present on these groups include one, two or three $R^{14}$ substituents as just described.

Optionally substituted polycycloaliphatic groups represented by $R^{15}$ include optionally substituted $C_{7-10}$bi- or tricycloalkyl or $C_{7-10}$bi- or tricyoalkenyl groups, for example norbornyl, norbornenyl or adamantyl groups. Polyheterocycloaliphatic groups include the polycycloalkyl groups just mentioned but with each group additionally containing one, two, three or four atoms or groups selected from those atoms and groups $L^4$ described above. Optional substituents which may be present on the polycycloaliphatic or polyheterocycloaliphatic groups include those just described for $R^{15}$ cycloaliphatic groups.

Optionally substituted aromatic or heteroaromatic groups represented by $R^{15}$ included those aromatic and heteroaromatic groups generally and specifically described below for the group $R^{11}$.

Optionally substituted aromatic groups represented by the group $R^{11}$ in compounds of the invention include for example monocyclic or bicyclic fused ring $C_{6-12}$ aromatic groups, such as phenyl, 1- or 2-naphthyl, 1- or 2-tetrahydronaphthyl, indanyl or indenyl groups, optionally substituted by one, two, three or more $R^{16}$ atoms or groups as defined below.

Heteroaromatic groups represented by the group Het or $R^{11}$ in the compounds of formula (1) include for example $C_{1-9}$ heteroaromatic groups containing for example one, two, three or four heteroatoms selected from oxygen, sulphur or nitrogen atoms. In general, the heteroaromatic groups may be for example monocyclic or bicyclic fused ring heteroaromatic groups. Monocyclic heteroaromatic groups include for example five- or six-membered heteroaromatic groups containing one, two, three or four heteroatoms selected from oxygen, sulphur or nitrogen atoms. Bicyclic heteroaromatic groups include for example nine- to thirteen-membered fused-ring heteroaromatic groups containing one, two or more heteroatoms selected from oxygen, sulphur or nitrogen atoms.

Particular examples of heteroaromatic groups of these types include pyrrolyl, furyl, thienyl, imidazolyl, N—$C_{1-6}$alkylimidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-thiadiazole, pyridyl, pyrimidinyl, pyridazinyl, pyrazinyl, 1,3,5-triazinyl, 1,2,4-triazinyl, 1,2,3-triazinyl, benzofuryl, [2,3-dihydro]benzofuryl, benzothienyl, benzotriazolyl, indolyl, isoindolyl, benzimidazolyl, imidazo[1,2-a]pyridyl, benzothiazolyl, benzoxazolyl, benzopyranyl, [3,4-dihydro]benzopyranyl, quinazolinyl, naphthyridinyl, pyrido[3,4-b]pyridyl, pyrido[3,2-b]pyridyl, pyrido[4,3-b]-pyridyl, quinolinyl, isoquinolinyl, tetrazolyl, 5,6,7,8-tetrahydroquinolinyl, 5,6,7,8-tetrahydroisoquinolinyl, and imidyl, e.g. succinimidyl, phthalimidyl, or naphthalimidyl such as 1,8-naphthalimidyl.

Optional substituents which may be present on the aromatic or heteroaromatic groups represented by $R^{11}$ include one, two, three or more substituents, each selected from an atom or group $R^{17}$ in which $R^{17}$ is —$R^{17a}$ or —Alk$^4(R^{17a})_m$, where $R^{17a}$ is a halogen atom, or an amino (—NH$_2$), substituted amino, nitro, cyano, amidino, hydroxyl (—OH), substituted hydroxyl, formyl, carboxyl (—CO$_2$H), esterified carboxyl, thiol (—SH), substituted thiol, —COR$^{18}$ [where $R^{18}$ is an —Alk$^3(R^{17a})_m$, aryl or heteroaryl group], —CSR$^{18}$, —SO$_3$H, —SO$_2$R$^{18}$ —SO$_2$NH$_2$, —SO$_2$NHR$^{18}$ SO$_2$N(R$^{18}$)$_2$, —CONH$_2$, —CSNH$_2$, —CONHR$^{18}$, —CSNHR$^{18}$, —CON[R$^{18}$]$_2$, —CSN(R$^{18}$)$_2$, —N(R$^{12}$) SO$_2$R$^{18}$, —N(SO$_2$R$^{18}$)$_2$, —NH(R$^{12}$)SO$_2$NH$_2$, —N(R$^{12}$) SO$_2$NHR$^{18}$, —N(R$^{12}$)SO$_2$N(R$^{18}$)$_2$, —N(R$^{12}$)COR$^{18}$, —N(R$^{12}$)CON(R$^{18}$)$_2$, —N(R$^{12}$)CSN(R$^{18}$)$_2$, —N(R$^{12}$) CSR$^{18}$, —N(R$^{12}$)C(O)OR$^{18}$, —SO$_2$NHet$^1$ [where —NHet$^1$ is an optionally substituted $C_{5-7}$cyclicamino group optionally containing one or more other —O— or —S— atoms or —N(R$^{12}$)—, —C(O)— or —C(S)— groups], —CONHet$^1$, —CSNHet$^1$, —N(R$^{12}$)SO$_2$NHet$^1$, —N(R$^{12}$)CONHet$^1$, —N(R$^{12}$)CSNHet$^1$, —SO$_2$N(R$^{12}$)Het$^2$ [where Het$^2$ is an optionally substituted monocyclic $C_{5-7}$carbocyclic group optionally containing one or more —O— or —S— atoms or —N(R$^{12}$)—, —C(O)— or —C(S)— groups], —CON(R$^{12}$) Het$^2$, —CSN(R$^{12}$)Het$^2$, —N(R$^{12}$)CON(R$^{12}$)Het$^2$, —N(R$^{12}$) CSN(R$^{12}$)Het$^2$, aryl or heteroaryl group; Alk$^4$ is a straight or branched $C_{1-6}$alkylene, $C_{2-6}$alkenylene or $C_{2-6}$alkynylene chain, optionally interrupted by one, two or three —O— or —S— atoms or —S(O)$_n$ [where n is an integer 1 or 2] or —N(R$^{19}$)-groups [where $R^{19}$ is a hydrogen atom or $C_{1-6}$alkyl, e.g. methyl or ethyl group]; and m is zero or an integer 1, 2 or 3. It will be appreciated that when two $R^{12}$ or $R^{18}$ groups are present in one of the above substituents, the $R^{12}$ or $R^{18}$ groups may be the same or different.

When in the group —Alk$^4$(R$^{17a}$)$_m$ m is an integer 1, 2 or 3, it is to be understood that the substituent or substituents $R^{17a}$ may be present on any suitable carbon atom in —Alk$^4$. Where more than one $R^{17a}$ substituent is present these may be the same or different and may be present on the same or different atom in —Alk$^4$. Clearly, when m is zero and no substituent $R^{17a}$ is present the alkylene, alkenylene or alkynylene chain represented by Alk$^4$ becomes an alkyl, alkenyl or alkynyl group.

When $R^{17a}$ is a substituted amino group it may be for example a group —NHR$^{18}$ [where $R^{18}$ is as defined above] or a group —N(R$^{18}$)$_2$ wherein each $R^{18}$ group is the same or different.

When $R^{17a}$ is a halogen atom it may be for example a fluorine, chlorine, bromine, or iodine atom.

When $R^{17a}$ is a substituted hydroxyl or substituted thiol group it may be for example a group —OR$^{18}$ or a —SR$^{18}$ or —SC(=NH)NH$_2$ group respectively.

Esterified carboxyl groups represented by the group $R^{17a}$ include groups of formula —CO$_2$Alk$^5$ wherein Alk$^5$ is a straight or branched, optionally substituted $C_{1-8}$alkyl group such as a methyl, ethyl, n-propyl, i-propyl, n-butyl, i-butyl, s-butyl or t-butyl group; a $C_{6-12}$aryl$C_{1-8}$alkyl group such as an optionally substituted benzyl, phenylethyl, phenylpropyl, 1-naphthylmethyl or 2-naphthylmethyl group; a $C_{6-12}$aryl group such as an optionally substituted phenyl, 1-naphthyl or 2-naphthyl group; a $C_{6-12}$aryloxy$C_{1-8}$alkyl group such as an optionally substituted phenyloxymethyl, phenyloxyethyl, 1-naphthyl-oxymethyl, or 2-naphthyloxymethyl group; an optionally substituted $C_{1-8}$alkanoyloxy$C_{1-8}$alkyl group, such as a pivaloyloxymethyl, propionyloxyethyl or propionyloxypropyl group; or a $C_{6-12}$aroyloxy$C_{1-8}$alkyl group such as an optionally substituted benzoyloxyethyl or benzoyloxypropyl group. Optional substituents present on the Alk$^5$ group include $R^{17a}$ substituents described above.

When Alk$^4$ is present in or as a substituent it may be for example a methylene, ethylene, n-propylene, i-propylene, n-butylene, i-butylene, s-butylene, t-butylene, ethenylene, 2-propenylene, 2-butenylene, 3-butenylene, ethynylene, 2-propynylene, 2-butynylene or 3-butynylene chain, optionally interrupted by one, two, or three —O— or —S—, atoms or —S(O)—, —S(O)$_2$— or —N(R$^{12}$)— groups.

Aryl or heteroaryl groups represented by the groups $R^{17a}$ or $R^{18}$ include mono- or bicyclic optionally substituted $C_{6-12}$ aromatic or $C_{1-9}$ heteroaromatic groups as described above for the group $R^{11}$. The aromatic and heteroaromatic groups may be attached to the remainder of the compound of formula (1) by any carbon or hetero e.g. nitrogen atom as appropriate.

When —NHet$^1$ or —Het$^2$ forms part of a substituent $R^{17}$ each may be for example an optionally substituted pyrrolidinyl, pyrazolidinyl, piperazinyl, morpholinyl, thiomorpholinyl, piperidinyl or thiazolidinyl group. Additionally Het$^2$ may represent for example, an optionally substituted cyclopentyl or cyclohexyl group. Optional substituents which may be present on —NHet$^1$ or —Het$^2$ include those $R^7$ substituents described above.

Particularly useful atoms or groups represented by $R^{17}$ include fluorine, chlorine, bromine or iodine atoms, or $C_{1-6}$alkyl, e.g. methyl, ethyl, n-propyl, i-propyl, n-butyl or t-butyl, optionally substituted phenyl, pyridyl, pyrrolyl, furyl, thiazolyl, or thienyl, $C_{1-6}$alkylamino, e.g. methylamino or ethylamino, $C_{1-6}$hydroxyalkyl, e.g. hydroxymethyl or hydroxyethyl, carboxy$C_{1-6}$alkyl, e.g. carboxyethyl, $C_{1-6}$alkylthio e.g. methylthio or ethylthio, carboxy$C_{1-6}$alkylthio, e.g. carboxymethylthio, 2-carboxyethylthio or 3-carboxy-propylthio, $C_{1-6}$alkoxy, e.g. methoxy or ethoxy, hydroxy$C_{1-6}$alkoxy, e.g. 2-hydroxyethoxy, optionally substituted phenoxy, pyridyloxy, thiazolyoxy, phenylthio or pyridylthio, $C_{5-7}$cycloalkoxy, e.g. cyclopentyloxy, halo$C_{1-6}$alkyl, e.g. trifluoromethyl, halo$C_{1-6}$alkoxy, e.g. trifluoromethoxy, $C_{1-6}$alkylamino, e.g. methylamino or ethylamino, amino (—NH$_2$), amino$C_{1-6}$alkyl, e.g. aminomethyl or aminoethyl, $C_{1-6}$dialkylamino, e.g. dimethylamino or diethylamino, $C_{1-6}$alkylamino$C_{1-6}$alkyl, e.g. ethylaminoethyl, $C_{1-6}$dialkylamino$C_{1-6}$alkyl, e.g. diethylaminoethyl, amino$C_{1-6}$alkoxy, e.g. aminoethoxy, $C_{1-6}$alkylamino$C_{1-6}$alkoxy, e.g. methylaminoethoxy, $C_{1-6}$dialkylamino$C_{1-6}$alkoxy, e.g. dimethylaminoethoxy, diethylaminoethoxy, isopropylaminoethoxy, or dimethylaminopropoxy, imido, such as phthalimido or naphthalimido, e.g. 1,8-naphthalimido, nitro, cyano, amidino, hydroxyl (—OH), formyl [HC(O)—], carboxyl (—CO$_2$H), —CO$_2$Alk$^5$ [where Alk$^5$ is as defined above], $C_{1-6}$ alkanoyl e.g. acetyl, optionally substituted benzoyl, thiol (—SH), thio$C_{1-6}$alkyl, e.g. thiomethyl or thioethyl, —SC(=NH)NH$_2$, sulphonyl (—SO$_3$H), $C_{1-6}$alkylsulphonyl, e.g. methylsulphonyl, aminosulphonyl (—SO$_2$NH$_2$), $C_{1-6}$alkylaminosulphonyl, e.g. methylaminosulphonyl or ethylaminosulphonyl, $C_{1-6}$dialkylaminosulphonyl, e.g. dimethylaminosulphonyl or diethylaminosulphonyl, phenylaminosulphonyl, carboxamido (—CONH$_2$), $C_{1-6}$alkylaminocarbonyl, e.g. methylaminocarbonyl or ethylaminocarbonyl, $C_{1-6}$dialkylaminocarbonyl, e.g. dimethylaminocarbonyl or diethylaminocarbonyl, amino$C_{1-6}$alkylaminocarbonyl, e.g. aminoethylaminocarbonyl, $C_{1-6}$dialkylamino$C_{1-6}$alkylamino-carbonyl, e.g. diethylaminoethylaminocarbonyl, aminocarbonylamino, $C_{1-6}$alkylaminocarbonylamino, e.g. methylaminocarbonylamino or ethylaminocarbonylamino, $C_{1-6}$dialkylaminocarbonylamino, e.g. dimethylaminocarbonylamino or diethylaminocarbonylamino, $C_{1-6}$alkylaminocabonyl$C_{1-6}$alkylamino, e.g. methylaminocarbonylmethylamino, aminothiocarbonylamino, $C_{1-6}$alkylaminothiocarbonylamino, e.g. methylaminothiocarbonylamino or ethylaminothiocarbonylamino, $C_{1-6}$dialkylaminothiocarbonylamino, e.g. dimethylaminothiocarbonylamino or diethylaminothiocarbonylamino, $C_{1-6}$alkylaminothiocarbonyl$C_{1-6}$alkylamino, e.g. ethylaminothiocarbonylmethylamino, —CONHC(=NH)NH$_2$, $C_{1-6}$alkylsulphonylamino, e.g. methylsulphonylamino or ethylsulphonylamino, $C_{1-6}$dialkylsulphonylamino, e.g. dimethylsulphonylamino or diethylsulphonylamino, optionally substituted phenylsulphonylamino, aminosulphonylamino (—NHSO$_2$NH$_2$), $C_{1-6}$alkylaminosulphonylamino, e.g. methylaminosulphonyl-amino or ethylaminosulphonylamino, $C_{1-6}$dialkylaminosulphonylamino, e.g. dimethylaminosulphonylamino or diethylaminosulphonylamino, optionally substituted morpholinesulphonylamino or morpholinesulphonyl$C_{1-6}$alkylamino, optionally substituted phenylaminosulphonylamino, $C_{1-6}$alkanoylamino, e.g. acetylamino, amino$C_{1-6}$alkanoylamino e.g. aminoacetylamino, $C_{1-6}$dialkylamino$C_{1-6}$alkanoylamino, e.g. dimethylaminoacetylamino, $C_{1-6}$alkanoylamino$C_{1-6}$alkyl, e.g. acetylaminomethyl, $C_{1-6}$alkanoylamino$C_{1-6}$alkylamino, e.g. acetamidoethylamino, $C_{1-6}$alkoxycarbonylamino, e.g. methoxycarbonylamino, ethoxycarbonylamino or t-butoxycarbonylamino or optionally substituted benzyloxy, pyridylmethoxy, thiazolylmethoxy, benzyloxycarbonylamino, benzyloxycarbonylamino$C_{1-6}$alkyl e.g. benzyloxycarbonylaminoethyl, benzothio, pyridylmethylthio or thiazolylmethylthio groups.

Where desired, two $R^{17}$ substituents may be linked together to form a cyclic group such as a cyclic ether, e.g. a $C_{1-6}$alkylenedioxy group such as methylenedioxy or ethylenedioxy.

It will be appreciated that where two or more $R^{17}$ substituents are present, these need not necessarily be the same atoms and/or groups. In general, the substituent(s) may be present at any available ring position in the aromatic or heteroaromatic group represented by $R^{11}$.

The presence of certain substituents in the compounds of formula (1) may enable salts of the compounds to be formed. Suitable salts include pharmaceutically acceptable salts, for example acid addition salts derived from inorganic or organic acids, and salts derived from inorganic and organic bases.

Acid addition salts include hydrochlorides, hydrobromides, hydroiodides, alkylsulphonates, e.g. methanesulphonates, ethanesulphonates, or isothionates, arylsulphonates, e.g. p-toluenesulphonates, besylates or napsylates, phosphates, sulphates, hydrogen sulphates, acetates, trifluoroacetates, propionates, citrates, maleates, fumarates, malonates, succinates, lactates, oxalates, tartrates and benzoates.

Salts derived from inorganic or organic bases include alkali metal salts such as sodium or potassium salts, alkaline earth metal salts such as magnesium or calcium salts, and organic amine salts such as morpholine, piperidine, dimethylamine or diethylamine salts.

Particularly useful salts of compounds according to the invention include pharmaceutically acceptable salts, especially acid addition pharmaceutically acceptable salts.

As noted above, the compounds of formula (1) may exist as geometric isomers. Thus, for example, one set of isomeric pairs of compounds of formula (1) is that wherein the $R^6$ and $R^{6a}$-containing groups are in a cis:

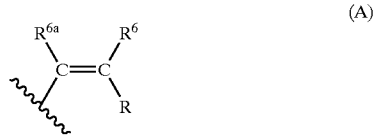

(A)

or trans relationship:

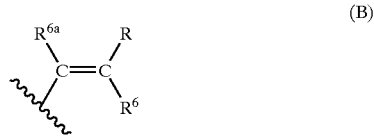

(B)

Although as explained previously the invention extends and relates to all geometric isomers of compounds of formla (1) certain of these isomers have particularly advantageous pharmacokinetic properties which makes them especially suitable for use in medicine. Thus, generally $R^6$ and $R^{6a}$ are preferably in a trans relationship to each other [(B) above] in the compounds of formula (1).

In the compounds according to the invention the group Het is preferably a monocyclic heteroaromatic group. Particularly useful groups of this type are five- or six-membered heteroaromatic groups as described previously for Het, especially five- or six-membered heteroaromatic groups containing one or two heteroatoms selected from oxygen, sulphur or nitrogen atoms. Nitrogen-containing groups are especially useful, particularly pyridyl or pyrimidinyl groups.

In general in compounds of the invention each of $R^1$, $R^2$ and $R^3$ is preferably a hydrogen atom or an optionally substituted alkyl, —$OR^8$, —$SR^8$, —$NR^8R^9$, —$COR^8$, —$CO_2R^8$, —$NO_2$ or —$CN$ group as defined herein.

In one preferred grop of comppounds of formula (1) $R^{6a}$ is a hydrogen atom.

A particularly useful group of compounds according to the invention has the formula (2):

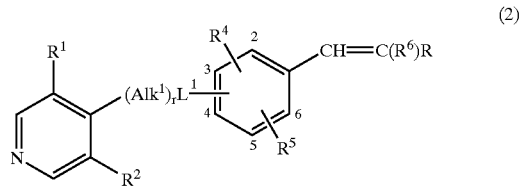

(2)

wherein $R^1$ and $R^2$, which may be the same or different is each an atom or group —$L^2(Alk^2)_tL^3(R^7)_u$ in which $L^2$, $Alk^2$, $t$, $L^3$, $R^7$ and $u$ are as defined for formula (1) provided that $R^1$ and $R^2$ are not both hydrogen atoms; $Alk^1$, $r$, $L^1$, $R^4$, $R^5$ and $R$ are as defined for formula (1); $R^6$ is an atom or group —$L^2(Alk^2)_tL^3R^{11}$ in which $L^2$, $L^3$, $Alk^2$ and $t$ are as previously defined and $R^{11}$ is a hydrogen or halogen atom or an —$OR^8$, —$NR^8R^9$, —$NO_2$, —$CN$, —$CO_2R^8$, —$CONR^8R^9$, —$COR^8$, —$N(R^8)COR^9$, —$N(R^8)CSR^9$, —$SO_2N(R^8)(R^9)$, —$N(R^8)SO_2R^8$, —$N(R^8)CON(R^9)(R^{10})$, —$N(R^8)CSN(R^9)(R^{10})$, —$N(R^8)SO_2N(R^9)(R^{10})$, or an optionally substituted aliphatic, heteroaliphatic, cycloaliphatic, heterocycloaliphatic, aromatic or heteroaromatic group;

and the salts, solvates, hydrates and N-oxides thereof.

In the compounds of formula (2) the $R^6$ and pyridyl-containing substituents preferably have a cis relationship as shown in (B) above.

$R^1$ and $R^2$ in compounds of formula (2) is each preferably as described above other than a hydrogen atom. Particularly useful $R^1$ and $R^2$ substituents in compounds of the invention include halogen atoms, especially fluorine or chlorine atoms, methyl, ethyl, methoxy, ethoxy, —$CF_3$, —OH, —CN, —$NO_2$, —$NH_2$, —$NHCH_3$, —$N(CH_3)_2$, —$COCH_3$, —$SCH_3$, —$CO_2H$ or —$CO_2CH_3$ groups.

R in the compounds of formulae (1) and (2) is preferably a —$CO_2H$ group.

When present, the aliphatic chain represented by $Alk^1$ in compounds of formulae (1) and (2) is preferably a —$CH_2$— chain.

In general in compounds of formulae (1) and (2) —$(Alk^1)_rL^1$— is preferably —$CH_2O$— or —$CON(R^{12})$—, and is especially a —CONH— group. The —$(Alk^1)_rL^1$— group is preferably attached to the 4-position of the phenyl ring containing the $R^4$ and $R^5$ substituents.

Particularly useful classes of compounds according to the invention are those wherein $R^6$ is a —$L^2R^{11}$ or —$L^2Alk^2R^{11}$ atom or group. In these classes, $L^2$ when present as a linker atom or group may especially be a —NHCO—, —NHCS— or —$NHSO_2$— group. $Alk^2$ when present may especially be a $C_{1-4}$alkylene chain. $R^{11}$ may especially be a hydrogen atom or an optionally substituted cycloaliphatic, heterocycloaliphatic, aromatic or heteroaromatic group as defined herein. Particularly useful $R^{11}$ groups include optionally substituted $C_{5-7}$cycloaliphatic, especially optionally substituted pyrrolidinyl, optionally substituted $C_{5-7}$heterocycloaliphatic, especially optionally substituted pyrrolidinyl or thiazolidinyl, optionally substituted phenyl and optionally substituted $C_{5-7}$heteroaromatic, especially optionally substituted pyridinyl groups. Optional substituents on these groups include in particular $R^{17}$ atoms or groups where the group is an aromatic or heteroaromatic group and $—(L^5)_p(Alk^3)_qR^{15}$ groups as described earlier where the group is a nitrogen-containing heterocycloaliphatic group such as a pyrrolidinyl or thiazolidinyl group. Particularly useful $(L^5)_p(Alk^3)_qR^{15}$ groups include $—L^5CH_2R^{15}$ groups in which $R^{15}$ is a hydrogen atom or an optionally substituted aromatic, particularly optionally substituted phenyl, or optionally substituted heteroaromatic, particularly optionally substituted pyridyl group as defined herein. In these groups $L^5$ may be as defined above, and is especially a $—C(O)—$ group.

Particularly useful compounds according to the invention include:

N-Acetyl-D-thioproline-4-[(3,5-dichloroisonicotinoyl) amino]-Z-didehydrophenylalanine;

N-Acetyl-D-thioproline-4-[(3,5-dichloroisonicotinoyl) amino]-E-didehydrophenylalanine;

N-Trimethylacetyl-4-[(3,5-dichloroisonicotinoyl)amino]-Z-didehydrophanylalanine;

N-Trimethylacetyl-4-[(3,5-dichloroisonicotinoyl)amino]-E-didehydrophenylalanine;

N-(2-Chloronicotinoyl)4-[(3,5-dichloroisonicotinoyl) amino]-Z-didehydrophenylalanine;

(Z)-3-{4-[(3,5-Dichloro-4-pyridinyl)methoxy]phenyl}-2-[(2,6-dimethoxybenzoyl)amino]-2-propenoic acid;

N-(2-Chloronicotinoyl)-4-[(3,5-dichloroisonicotinoyl) amino]-E-didehydrophenylalanine;

and the salts, solvates, hydrates and N-oxides thereof.

Compounds according to the invention are potent and selective inhibitors of α4 integrins. The ability of the compounds to act in this way may be simply determined by employing tests such as those described in the Examples hereinafter. In particular compounds of the invention, such as the compounds of formula (1a) herein, are advantageously selective $\alpha4\beta_1$ inhibitors.

The compounds are of use in modulating cell adhesion and in particular are of use in the prophylaxis and treatment of diseases or disorders involving inflammation in which the extravasation of leukocytes plays a role and the invention extends to such a use and to the use of the compounds for the manufacture of a medicament for treating such diseases or disorders.

Diseases or disorders of this type include inflammatory arthritis such as rheumatoid arthritis vasculitis or polydermatomyositis, multiple sclerosis, allograft rejection, diabetes, inflammatory dermatoses such as psoriasis or dermatitis, asthma and inflammatory bowel disease.

For the prophylaxis or treatment of disease the compounds according to the invention may be administered as pharmaceutical compositions, and according to a further aspect of the invention we provide a pharmaceutical composition which comprises a compound of formula (1) together with one or more pharmaceutically acceptable carriers, excipients or diluents.

Pharmaceutical compositions according to the invention may take a form suitable for oral, buccal, parenteral, nasal, topical or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles and preservatives. The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds for formula (1) may be formulated for parenteral administration by injection e.g. by bolus injection or infusion. Formulations for injection may be presented in unit dosage form, e.g. in glass ampoule or multi dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (1) may also be formulated as a depot preparation. Such long acting formulations may be administered by implantation or by intramuscular injection.

For nasal administration or administration by inhalation, the compounds for use according to the present invention are conveniently delivered in the form of an aerosol spray presentation for pressurised packs or a nebuliser, with the use of suitable propellant, e.g. dichlorodifluoromethane, trichlorofluoromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

The quantity of a compound of the invention required for the prophylaxis or treatment of a particular condition will vary depending on the compound chosen, and the condition of the patient to be treated. In general, however, daily dosages may range from around 100 ng/kg to 100 mg/kg e.g. around 0.01 mg/kg to 40 mg/kg body weight for oral or buccal administration, from around 10 ng/kg to 50 mg/kg body weight for parenteral administration and around 0.05 mg to around 1000 mg e.g. around 0.5 mg to around 1000 mg for nasal administration or administration by inhalation or insufflation.

The compounds of the invention may be prepared by a number of processes as generally described below and more specifically in the Examples hereinafter. In the following process description, the symbols $R^1$–$R^6$ and $R^{6a}$, $L^1$, $Alk^1$ and r when used in the formulae depicted are to be understood to represent those groups described above in relation to formula (1) unless otherwise indicated. In the reactions described below, it may be necessary to protect reactive functional groups, for example hydroxy, amino, thio or carboxy groups, where these are desired in the final product, to avoid their unwanted participation in the reactions. Conventional protecting groups may be used in accordance with standard practice [see, for example, Green, T. W. in "Protective Groups in Organic Synthesis", John Wiley and Sons, 1991]. In some instances, deprotection may be the final step in the synthesis of a compound of formula (1) and the processes according to the invention described hereinafter are to be understood to extend to such removal of protecting groups. For convenience the processes described below all refer to a preparation of a compound of formula (1) but clearly the description applies equally to the preparation of compounds of formulae (1a) and (2).

Thus according to a further aspect of the invention, a compound of formula (1) in which R is a —$CO_2H$ group may be obtained by hydrolysis of an ester of formula (3):

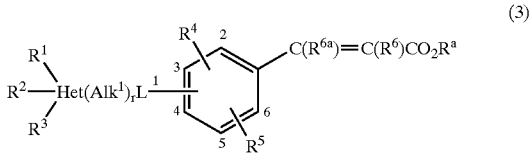

(3)

where $R^a$ is an alkyl group, for example a $C_{1-6}$alkyl group as described above.

The hydrolysis may be performed using either an acid or a base depending on the nature of $R^a$, for example an organic acid such as trifluoroacetic acid or an inorganic base such as lithium or potassium hydroxide optionally in an aqueous organic solvent such as an amide, e.g. a substituted amide such as dimethylformamide, an ether, e.g. a cyclic ether such as tetrahydrofuran or dioxane or an alcohol, e.g. methanol at around ambient temperature. Where desired, mixtures of such solvents may be used.

Esters of formula (3) and, in general, esters of formula (1) in which R is a —$CO_2Alk^5$ group may be prepared by reaction of an aldehyde or ketone of formula (4):

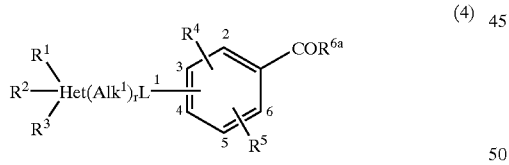

(4)

with a phosphonate $(Alk^6O)_2P(O)CH(R^6)CO_2Alk^5$, where $Alk^6$ is a $C_{1-6}$alkyl group optionally substituted by one or more fluorine atoms, in the presence of a base.

Suitable bases include organometallic bases, for example an organolithium compound such as n-butyllithium or lithium diisopropylamide, hydrides such as sodium or potassium hydride, alkoxides, such as sodium alkoxides, e.g. sodium methoxide, and cyclic amines, for example 1,8-diazabicyclo[5.4.0]undec-7-ene.

The reaction may be performed in a suitable solvent, for example a polar aprotic solvent such as an amide, e.g. N,N-dimethylformamide; or a non-polar solvent such as an ether, e.g. a cyclic ether such as tetrahydrofuran or a halogenated hydrocarbon, e.g. dichloromethane. Preferably the react ion is carried out at a low temperature for example from around −78° C. to around ambient temperature.

Intermediate phosphonates of formula $(Alk^6O)_2P(O)CH(R^6)CO_2Alk^5$ are either known compounds or may be obtained by reaction of a halide $HalCH(R^6)CO_2Alk^5$ [where Hal is a halogen atom such as a chlorine or bromine atom] with a phosphite $P(OAlk^6)_3$. The halides $HalCH(R^6)CO_2Alk^5$ are either known compounds or may be prepared by manipulation of known compounds by the standard substitution, oxidation, reduction and/or cleavage reactions described hereinafter. In general the reaction with the phosphite $P(OAlk^6)_3$ may be carried out at any stage in the synthesis of the desired phosphonate $(Alk^6O)_2P(O)CH(R^6)CO_2Alk^5$.

Intermediate aldehydes of formula (4) are either known compounds or may be prepared by simple chemical manipulation of known compounds.

Thus, for example, the aldehydes [where $R^{6a}$ is a hydrogen atom] may be obtained by oxidation of the corresponding alcohols [in which —$COR^{6a}$ is replaced by a —CHOH group] using an oxidising agent such as manganese (IV) oxide in a solvent such as dichloromethane.

Intermediate ketones of formula (4) [where $R^{6a}$ is other than a hydrogen atom] may also be obtained by oxidation of the corresponding alcohol of formula (4), using for example manganese (IV) oxide in a solvent such as dichloromethane, or by reaction of a corresponding halide [in which —$COR^{6a}$ has been replaced by a halogen atom such as a bromine or chlorine atom] by halogen-metal exchange with a base such as n-butyllithium followed by reaction with a nitrile $R^{6a}CN$, an acid chloride $R^{6a}COCl$ or an ester $R^{6a}CO_2R^a$, in a solvent such as tetrahydrofuran, at a low temperature e.g. around −70° C. and subsequent treatment with an acid such as hydrochloric acid at around ambient temperature.

In another process, esters or amides of formula (1), for example where R is a carboxylic acid ester or amide, and in which $R^6$ or $R^{6a}$ is a hydrogen atom, may be prepared by coupling an organpalladium compound derived from an intermediate of formula (5):

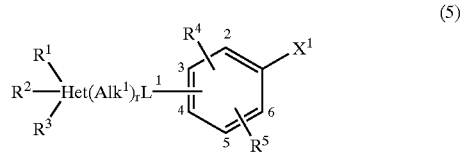

(5)

[in which $X^1$ is a halogen atom such as an iodine atom or is a trifluoromethylsulphonyloxy group] and a palladium salt with an ester or amide $R^{6a}CHCHR$ or $CH_2C(R^6)R$ where R is as just defined in the presence of a base.

Suitable palladium salts include palladium acetate or palladium chloride. Where palladium acetate is used the reaction for example may be carried out under phase-transfer conditions in the presence of tetra-n-butylammonium bromide and an alkali-metal base such as sodium bicarbonate in dimethylformamide. In another example, the reaction may be performed using palladium acetate or palladium chloride and a phosphine, for example a triarylphosphine such as triphenylphosphine, and a base such as triethylamine, at for example an elevated temperature and pressure.

Where desired, the starting materials in the above general coupling reaction may be varied. The reaction may thus be performed using an ester or amide of formula (1) in which R is a carboxylic acid ester or amide and $R^6$ and $R^{6a}$ is each a hydrogen atom with a reagent $R^{6b}X^1$ in which $R^{6b}$ is an aromatic or heteroaromatic group and $X^1$ is as defined above. Similarly the reaction may be used to generate intermediates to the final compounds described herein, for example intermediate esters of formula (3) by using the appropriate alkene ester and a reagent $R^{6b}X^1$.

Where necessary, the intermediate aldehydes and ketones of formula (4) and the corresponding alcohols and halides described above, as well as the intermediates of formula (5) and the esters or amides $R^{6a}CHCHR$ or $CH_2C(R^6)R$ may be obtained from simpler aromatic or heteroaromatic compounds by one or more standard synthetic methods employing substitution, oxidation, reduction or cleavage reactions. Particular substitution approaches include conventional alkylation, arylation, heteroarylation, acylation, thioacylation, halogenation, sulphonylation, nitration, formylation and coupling procedures. It will be appreciated that these methods may also be used to modify the compounds of formula (1) and the esters (3) where appropriate functional groups exist in these compounds and to generate suitable phosphonates $(Alk^6O)_2P(O)CH(R^6)CO_2Alk^5$ for example to obtain desired groups —$CH(R^6)CO_2Alk^5$ therein.

Thus compounds of the invention and intermediates thereto may be prepared by alkylation, arylation or heteroarylation. For example, compounds containing a —$L^1H$, —$L^2H$, or —$L^3H$ group (where $L^1$, $L^2$ and $L^3$ (is each a linker atom or group) may be treated with an alkylating agent:

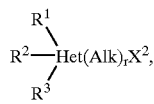

$R^{11}L^3(Alk^2)_rX^2$ or $R^{11}X^2$ in which $X^2$ is a leaving atom or group such as a halogen atom, e.g. a fluorine, bromine, iodine or chlorine atom or a sulphonyloxy group such as an alkylsulphonyloxy, e.g. trifluoromethylsulphonyloxy or arylsulphonyloxy, e.g. p-toluenesulphonyloxy group.

The reaction may be carried out in the presence of a base such as a carbonate, e.g. caesium or potassium carbonate, an alkoxide, e.g. potassium t-butoxide, or a hydride, e.g. sodium hydride, in a dipolar aprotic solvent such as an amide, e.g. a substituted amide such as dimethylformamide or an ether, e.g. a cyclic ether such as tetrahydrofuran.

In another example, compounds containing a —$L^1H$, —$L^2H$ or —$L^3H$ group as defined above may be functionalised by acylation or thioacylation, for example by reaction with one of the alkylating agents just described but in which $X^2$ is replaced by a —$C(O)X^3$, $C(S)X^3$, —$N(R^8)COX^3$ or —$N(R^8)C(S)X^3$ group in which $X^3$ is a leaving atom or group as described for $X^2$. The reaction may be performed in the presence of a base, such as a hydride, e.g. sodium hydride or an amine, e.g. triethylamine or N-methylmorpholine, in a solvent such as a halogenated hydrocarbon, e.g. dichloromethane or carbon tetrachloride or an amide, e.g. dimethylformamide, at for example ambient temperature. Alternatively, the acylation or thioacylation may be carried out under the same conditions with an acid or thioacid (for example one of the alkylating agents described above in which $X^2$ is replaced by a —$CO_2H$ or —COSH group) in the presence of a condensing agent, for example a diimide such as 1-(3-dimethylaminopropyl)-3-ethylcarbodiimide or N,N'-dicyclohexylcarbodiimide, advantageously in the presence of a catalyst such as a N-hydroxy compound e.g. a N-hydroxytriazole such as 1-hydroxybenzotriazole.

Alternatively the acid may be reacted with a chloroformate, for example ethylchloroformate, prior to the desired acylation reaction In a further example compounds may be obtained by sulphonylation of a compound containing an —OH group by reaction with one of the above alkylating agents but in which $X^2$ is replaced by a —$S(O)Hal$ or —$SO_2Hal$ group in which Hal is a halogen atom such as chlorine atom] in the presence of a base, for example an inorganic base such as sodium hydride in a solvent such as an amide, e.g. a substituted amide such as dimethylformamide at for example ambient temperature.

In another example, compounds containing a —$L^1H$, —$L^2H$ or —$L^3H$ group as defined above may be coupled with one of the alkylation agents just described but in which X is preplaced by an —OH group in a solvent such as tetrahydrofuran in the presence of a phosphine, e.g. triphenylphosphine and an activator such as diethyl, diisopropyl- or dimethylazodicarboxylate.

In a further example, ester groups —$CO_2R^8$ or —$CO_2Alk^5$ in the compounds may be converted to the corresponding acid [—$CO_2H$] by acid- or base-catalysed hydrolysis depending on the nature of the groups $R^8$ or $Alk^5$. Acid- or base-catalysed hydrolysis may be achieved for example by treatment with an organic or inorganic acid, e.g. trifluoroacetic acid in an aqueous solvent or a mineral acid such as hydrochloric acid in a solvent such as dioxan or an alkali metal hydroxide, e.g. lithium hydroxide in an aqueous alcohol, e.g. aqueous methanol.

In a second example, —$OR^8$ or —$OR^{18}$ groups [where $R^8$ or $R^{18}$ each represents an alkyl group such as methyl group] in compounds of formula (1) may be cleaved to the corresponding alcohol —OH by reaction with boron tribromide in a solvent such as a halogenated hydrocarbon, e.g. dichloromethane at a low temperature, e.g. around −78° C.

Alcohol [—OH] groups may also be obtained by hydrogenation of a corresponding —$OCH_2R^{18}$ group (where $R^{18}$ is an aryl group) using a metal catalyst, for example palladium on a support such as carbon in a solvent such as ethanol in the presence of ammonium formate, cyclohexadiene or hydrogen, from around ambient to the reflux temperature. In another example, —OH groups may be generated from the corresponding ester [—$CO_2Alk^5$ or $CO_2R^8$] or aldehyde [—CHO] by reduction, using for example a complex metal hydride such as lithium aluminium hydride or sodium borohydride in a solvent such as methanol.

In another example, alcohol —OH groups in the compounds may be converted to a corresponding —$OR^8$ group by coupling with a reagent $R^8OH$ in a solvent such as tetrahydrofuran in the presence of a phosphine, e.g. triphenylphosphine and an activator such as diethyl-, dilsopropyl-, or dimethylazodicarboxylate.

Aminosulphonylamino [—$NHSO_2NH_2$] groups in the compounds may be obtained, in another example, by reaction of a corresponding amine [—$NH_2$] with sulphamide in the presence of an organic base such as pyridine at an elevated temperature, e.g. the reflux temperature.

In a further example amine (—$NH_2$) groups may be alkylated using a reductive alkylation process employing an aldehyde and a borohydride, for example sodium triacetoxyborohyride or sodium cyanoborohydride, in a solvent such as a halogenated hydrocarbon, e.g. dichloromethane, a ketone such as acetone, or an alcohol, e.g. ethanol, where necessary in the presence of an acid such as acetic acid at around ambient temperature.

In a further example, amine [—$NH_2$] groups in compounds of formula (1) may be obtained by hydrolysis from a corresponding imide by reaction with hydrazine in a solvent such as an alcohol, e.g. ethanol at ambient temperature.

In another example, a nitro [—NO$_2$] group may be reduced to an amine [—NH$_2$], for example by catalytic hydrogenation using for example hydrogen in the presence of a metal catalyst, for example palladium on a support such as carbon in a solvent such as an ether, e.g. tetrahydrofuran or an alcohol e.g. methanol, or by chemical reduction using for example a metal, e.g. tin or iron, in the presence of an acid such as hydrochloric acid in a solvent such as ethanol at an elevated temperature Reduction, for example using a metal and reaction conditions as just described, may also be used to obtain a compound in which L$^2$ is a —NHCO— group from the corresponding oxazolone in which L is

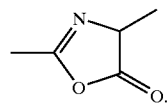

The oxazolone may be prepared by reaction of an appropriate amino acid or a reactive derivative thereof and a ketone in the presence of a catalyst, for example a lead salt such as lead acetale, in a solvent such as tetrahydrofuran at an elevated temperature.

Aromatic halogen substituents in the compounds may be subjected to halogen-metal exchange with a base, for example a lithium base such as n-butyl or t-butyl lithium, optionally at a low temperature, e.g. around −78° C., in a solvent such as tetrahydrofuran and then quenched with an electrophile to introduce a desired substituent. Thus, for example, a formyl group may be introduced by using dimethylformamide as the electrophile; a thiomethyl group may be introduced by using dimethyidisulphide as the electrophile.

In a further example, compounds in which R$^{6a}$ is an aromatic group may be prepared by reaction of a corresponding compound in which R$^{6a}$ is a halogen atom such as a bromine atom with a boronic acid R$^{6a}$B(OH)$_2$ [where R$^{6a}$ is an aromatic group] in the presence of a complex metal catalyst. Suitable catalysts include heavy metal catalysts, for example palladium catalysts, such as tetrakis (triphenylphosphine)palladium. The reaction may be performed in an inert organic solvent, for example an ether such as dimethoxyethane or dioxane, in the presence of a base, e.g. an alkali carbonate such as sodium carbonate, at an elevated temperature, e.g. the reflux temperature.

In another example, sulphur atoms in the compounds, for example when present in a linker group L$^1$, L$^2$ or L$^3$ may be oxidised to the corresponding sulphoxide or sulphone using an oxidising agent such as a peroxy acid, e.g. 3-chloroperoxybenzoic acid, in an inert solvent such as a halogenated hydrocarbon, e.g. dichloromethane, at around ambient temperature.

N-oxides of compounds of formula (1) may be prepared for example by oxidation of the corresponding nitrogen base using an oxidising agent such as hydrogen peroxide in the presence of an acid such as acetic acid, at an elevated temperature, for example around 70° C. to 80° C., or alternatively by reaction with a peracid such as peracetic acid in a solvent, e.g. dichloromethane, at ambient temperature.

Salts of compounds of formula (1) may be prepared by reaction of a compound of formula (1) with an appropriate base in a suit able solvent or mixture of solvents e.g. an organic solvent such as an ether e.g. diethylether, or an alcohol, e.g. ethanol using conventional procedures.

Where it is desired to obtain a particular enantiomer of a compound of formula (1) this may be produced from a corresponding mixture of enantiomers using any suitable conventional procedure for resolving enantiomers.

Thus for example diastereomeric derivatives, e.g. salts, may be produced by reaction of a mixture of enantiomers of formula (1) e.g. a racemate, and an appropriate chiral compound, e.g. a chiral base. The diastereomers may then be separated by any convenient means, for example by crystallisation and the desired enantiomer recovered, e.g. by treatment with an acid in the instance where the diastereomer is a salt.

In another resolution process a racemate of formula (1) may be separated using chiral High Performance Liquid Chromatography. Alternatively, if desired a particular enantiomer may be obtained by using an appropriate chiral intermediate in one of the processes described above.

Chromatography, recrystalliation and other conventional separation procedures may also be used with intermediates or final products where it is desired to obtain a particular geometric isomer of the invention.

The following Examples illustrate the invention. All temperatures are in °C. The following abbreviations are used:

DMF—dimethylformamide;
DMSO—dimethylsulphoxide;
HOBT—1-hydroxybenzotriazole;
THF—tetrahydrofuran;
NMM—N-methylmorpholine;
EtOAc—ethyl acetate;
MeOH—methanol;
LDA—lithium diisopropylamide
Ar—aryl;
py—pyridine;
Me—methyl;
Bu—butyl;
DBU—1,8-diazabicyclo[5.4.0]undec-7-ene;
DME—dimethoxyethane
All NMR's were obtained at 300 mHz.

INTERMEDATE 1

N-Acetyl-D-thioproline-α-phosphonogycline Trimethyl Ester

A mixture of N-(benzyloxycarbonyl)-α-phosphonoglycine trimethyl ester (5 g, 15 mmol) and palladium on charcoal (10% Pd, 500 mg) in methanol (50 ml) was stirred under a hydrogen atmosphere (balloon) at room temperature for 4 h. The mixture was filtered through Celite® and the filtrate evaporated under reduced pressure to give the corresponding amine. A mixture of this amine, N-acetyl thioproline (2.63 g, 15 mmol), HOBT (2.23 g, 16.5 mmol) and NMM (1.81 ml, 16.5 mmol) was dissolved in CH$_2$Cl$_2$ (75 ml). EDC (3.17 g, 16.5 mmol) was added and the mixture stirred overnight at room temperature. It was then diluted with CH$_2$Cl$_2$ (200 ml) and washed with aqueous HCl (1M, 50 ml), saturated NaHCO$_3$ (50 ml) and water (50 ml), dried (Na$_2$SO$_4$) and evaporated under reduced pressure. Purification of the residue by column chromatography (SiO$_2$; CH$_2$Cl$_2$/MeOH, 93:7) gave the title compound as a colourless gum (2.79 g, 53%). δH (DMSO-d$^6$) (spectrum complex due to presence of rotamers and diastereoisomers) 9.2 (br m) and 8.9 (br m) together (1 H, CONH), 5.75–492 (2H, m, 2×CH$_α$), 4.74 (d, J 8.8 Hz) and 4.73 (d, J 9.7 Hz) and 4.53 (d, J 8.6 HZ) and 4.52 (d, J 8.6 Hz) and 4.32 (d. J 9.7 Hz) and 4.31 (d, J 9.8 Hz) together (2H, NCH$_2$S), 3.74–3.67 (several S, 9H, CO$_2$Me+P(OMe)$_2$), 3.49 (dd, J 7.3, 11.8 Hz) and 3.35–3.26 (m) and 3.14–3.07 (m) and 2.97 (dd, J 4.4, 11.9 Hz) together (2H, CHC$\underline{H}_2$S), 2.061 (s) and 2.057 (s) and 1.92 (s) and 1.91 (s) together (3H, NCOCH$_3$); m/z (ESI, 60V) 355 (M$^+$+1).

INTERMEDIATE 2

3,5-Dichloro-N$^4$-(4-formylphenyl)isonicotinamide

A mixture of 3,5-dichloroisonicotinic acid (2.88 g, 15 mmol) and thionyl chloride (30 ml) was heated to reflux. A few drops of DMF were added and the suspension refluxed for 2 h to give a slightly yellow solution. Excess reagent was removed under reduced pressure and the residue azeotroped with toluene (2×50 ml) to give 3,5-dichloroisonicotinoyl chloride. This was dissolved in CH$_2$Cl$_2$ (50 ml) and added to a solution of 4-aminobenzyl alcohol (1.60 g, 13 mmol) and NMM (1.65 ml, 15 mmol) in CH$_2$Cl$_2$ (50 ml). The mixture was stirred at room temperature overnight. Manganese IV oxide (activated, <5 micron, ~85%, 22 g) was added to the resulting suspension. The mixture was stirred at room temperature for 6 h then filtered through Celite®. The filtrate was washed with dilute hydrochloric acid (1M, 50 ml) and saturated aqueous sodium hydrogen carbonate (50 ml), dried (Na$_2$SO$_4$) and evaporated under reduced pressure to give the title compound (2.40 g, 63%) as a pale yellow solid. δH (DMSO-d$^6$) 11.35 (1H, s, CHO), 9.95 (1H, s, CONH), 8.83 (2H, s, pyH), 7.96 (2H, d, J 8.7 Hz, ArH) and 7.88 (2H, d, J 8.7 Hz, ArH); m/z (ESI, 60V) 295 (M$^+$+1).

INTERMEDIATE 3

N-(Trimethylacetyl)-α-phosphonoglycine Trimethyl Ester

A mixture of N-(benzyloxycarbonyl)-α-phosphonoglycine trimethyl ester (Aldrich, 5 g, 15 mmol) and palladium on charcoal (10% pd, 1.0 g) in methanol 60 ml) was stirred under a hydrogen atmosphere (balloon) at room temperature for 2 h. The mixture was filtered through Celite® and the filtrate evaporated under reduced pressure to give the corrsponding amine. This amine was dissolved in CH$_2$Cl$_2$ (75 ml) at 0°. NMM (1.65 ml, 15 mmol) and trimethylacetyl chloride (1.85 ml, 15 mmol) were added and the mixture stirred at room temperature overnight. The mixture was diluted with CH$_2$Cl$_2$ (300 ml), washed with dilute hydrochloric acid (1M, 50 ml) and saturated aqueous sodium hydrogen carbonate (50 ml), dried (Na$_2$SO$_4$) and evaporated under reduced pressure to give the title compound as a white waxy solid (4.0 g, 95%). δH (DMSO-d$^6$) 8.08 (1H, br d, J 8.9 Hz, CONH), 5.15 (1H, dd, J 23.7, 9.0 Hz, CHα), 3.73–3.67 (9H, m, CO$_2$Me+P(OMe)$_2$) and 1.14 (9H, s, Me$_3$CCO); m/z (ESI, 60V) 282 (M$^+$+1).

INTERMEDIATE 4

N-(2-Chloronicotinoyl)-α-phosphonoglycine Trimethyl Ester

A mixture of N-(benzyloxycarbonyl)-α-phosphonoglycine trimethyl ester (Aldrich, 4.86 g, 14.7 mmol) and palladium on charcoal (10% Pd, 2 g) in MeOH (60 ml) was stirred under a hydrogen atmosphere (balloon) for 4 h. The mixture was filtered through Celite® and the filtrate evaporated under reduced pressure to give the corresponding amine. 2-Chloronicotinoyl chloride (14.7 mmol, 2.59 g) was added to a solution of the amine and NMM (1.65 ml, 15 mmol) in CH$_2$Cl$_2$ (75 ml) at 0°. The mixture was stirred overnight at room temperature, diluted with CH$_2$Cl$_2$ (300 ml), washed with dilute hydrochloric acid (50 ml) and saturated NaHCO$_3$ (50 ml), dried (Na$_2$SO$_4$) and evaporated under reduced pressure to give the title compound as a colourless viscous gum (4.54 g, 91%). δH (DMSO-d$^6$) 9.67 (1H, dd, J 8.9, 2.8 Hz, CONH), 8.49 (1H, dd, J 4.8, 2.0 Hz, ArH), 7.82 (1H, dd, J 7.5, 2.0 Hz, ArH), 7.50 (1H, dd, J 7.5, 4.8 Hz), 5.28 (1H, dd, J 22.9, 8.9 Hz, CHα) and 3.82–3.73 (9H, m, CO$_2$Me+P(OMe)$_2$); m/z (ESI, 60V) 337 (M$^+$+1).

INTERMEDIATE 5

2-(2-Chloro-3-pyridinyl)-4-[(Z)-1-(4-nitrophenyl) ethylidene]-1,3-oxazol-5-one

A mixture of 2-{[(2-chloro-3-pyridinyl)carbonyl] amino}acetic acid (6.44 g, 30 mmol, prepared from glycine and 2-chloronicotinoyl chloride), 4-nitroacetophenone (2.48 g, 15 mmol), lead (IV) acetate (3.33 g, 7.5 mmol) and acetic anhydride in THF (30 ml) was heated at reflux for 4 days. The mixture was poured onto crushed ice, the solid filtered off, washed with water and dried. The brown solid was triturated twice with boiling ethanol and filtered off to give the title compound as a brown solid (1.07 g). δ$_H$ (CDCl$_3$), 8.57 (1H, dd, J 4.8, 2.1 Hz, PyH), 8.34–8,29 (3H, m, ArH+PyH), 8.05 (2H, d, J 9.1 Hz, ArH), 7.41 (1H, dd, J 7.9, 4.8 Hz, PyH) and 2.84 (3H, s, Me).

INTERMEDIATE 6

Ethyl (Z)-3-(4-Aminophenyl)-2-{[(2-chloro-3-pyridinyl)carbonyl]amino}-2-butenoate A mixture of Intermediate 5 (840 mg, 2.45 mmol) and tin(II) chloride dihydrate (2.76 g, 12.2 mmol) in ethanol (50 ml) was heated at reflux for 2 h. The solvent was removed in vacuo. CH$_2$Cl$_2$ (100 ml) was added to the residue and the resulting suspension treated with sodium carbonate (50 ml). The mixture was filtered and the filtrate extracted with CH$_2$Cl$_2$ (100 ml). The organic extract was dried (Na$_2$SO$_4$) and evaporated in vacuo. Chromatography (SiO$_2$; CH$_2$Cl$_2$/MeOH, 95:5) gave the title compound as a yellow foam (213 mg) (also contained some of the E isomer, Z:E 85:15 determined by HNMR). δ$_H$ (CDCl$_3$), 8.41 (1H, dd, J 4.7, 2.0 Hz, PyH), 8.03 (1H, dd, J 7.7, 2.0 Hz, PyH), 7.65 (1H, br s, CONH), 7.29 (1H, dd, J 7.7, 4.8 Hz, PyH), 7.11 (2H, d, J 8.6 Hz, PyH), 6.65 (2H, d,J 8.6 Hz, ArH), 4.34 (2H, q, J 7.1 Hz, CO$_2$C$\underline{H}_2$CH$_3$), 3.77 (2H, v br s, NH$_2$), 2.32 (3H, s, Me) and 1.35 (3H, t, J 7.1 Hz, CO$_2$CH$_2$C$\underline{H}_3$); m/z (ESI, 60V) 360 (MH$^+$).

INTERMEDIATE 7

4-[(3,5-Dichloro-4-pyridinyl)methoxy]benzaldehyde

A mixture of 4-(bromomethyl)-3,5-dichloropyridine (15 g, 62.2 mmol), 4-hydroxybenzaldehyde (7.97 g, 65.4 mmol) and caesium carbonate (22.3 g, 68.5 mmol) in DMF (150 ml) was stirred for 4.5 h at room temperature. The mixture was poured into water and extracted with EtOAc. The organic extract was washed with sodium carbonate solution (×2) and brine, dried (MgSO$_4$) and evaporated in vacuo to give the title compound as a brown solid (16 g). δ$_H$(DMSO-d$^6$), 9.91 (1H, s), 8.74 (2H, s), 7.91 (2H, d, J 8.6 Hz), 7.27 (2H, d, J 8.6 Hz), 5.37 (2H, s); m/z (ESI) 282 (MH$^+$).

INTERMEDIATE 8

Methyl 2-(Diethoxyphosphino)-2-[(2,6-dimethoxybenzoyl)amino]acetate 2,6-Dimethoxybenzoyl chloride (1.28 g, 6.42 mmol) was added to a mixture of methyl 2-amino-2-

(diethoxyphosphino)acetate hydrochloride [1.5 g, 6.11 mmol, prepared by the method of Y. Nasukawa, et al, J. Org. Chem, (1992) 57, 5453] and NMM (1.5 ml, 13.44 mmol) in $CH_2Cl_2$ (30 ml). The mixture was stirred overnight at room temperatue then poured into 10% citric acid. The mixture was extracted with $CH_2Cl_2$ (×2) and the combined organic extracts washed with sodium hydrogen carbonate solution (×2) and brine, dried ($MgSO_4$) and evaporated in vacuo to give a brown solid (1.62 g). $\delta_H$ (DMSO-d$^6$) 8.82 (1H, dd, J 9.1, 2.5 Hz), 7.29 (1H, t, J 8.4 Hz), 6.65 (2H, d, J 8.4 Hz), 5.20 (1H, dd, J 20.0, 9.2 Hz), 4.15–4.03 (4H, m), 3.72 (3H, s), 3.71 (6H, s), 1.39–1.20 (6H, m); m/z (ESI) 390 (MH$^+$).

EXAMPLE 1

N-Acetyl-D-thioproline-4-[(3,5-dichloroisonicotinoyl)amino]-Z-didehydrophenylalanine Methyl Ester DBU (173 μl, 1.15 mmol) was added to a solution of Intermediate 1 (407 mg, 1.15 mmol) and Intermediate 2 (339 mg, 1.15 mmol) in $CH_2Cl_2$ (12 ml). The mixture was stirred at room temperature overnight then diluted with $CH_2Cl_2$ (100 ml), washed with dilute hydrochloric acid (1M, 30 ml), dried ($Na_2SO_4$) and evaporated under reduced pressure. Column chromatrography (SiO$_2$; EtOAc/MeOH, 98:2) gave the title compound as a white foam (555 mg, 92%) contaminated with a few percent of its double bond isomer (by NMR). Crystallization from EtOAc gave the pure title compound as poorly formed white crystals (400 mg) m.p. 155–158°. δH (DMSO-d$^6$, 390K) 9.2 (1H, b r s, CHCON$\underline{H}$), 8.71 (2H, s, PyH), 7.67 (4H, s, ArH), 7.34 (1H, s C=CH), 4.99 (1H, dd, J 7.3, 4.0 Hz, CHαthiopro), 4.81 (1H, d, J 9.1 Hz, NC$\underline{H}_A$H$_B$S), 4.54 (1H, d, J 9.1 Hz, NCH$_A$$\underline{H}_B$S), 3.75 (3H, s, CO$_2$Me), 3.41 (1H, dd, J 11.6, 7.3 Hz, CHC$\underline{H}_A$H$_B$S), 3.26 (1H, dd, J 11.6, 3.9 Hz, CHCH$_A$$\underline{H}_B$S) and 2.11 (3H, s, COCH$_3$) (pyCONH not observed); m/z (ESI, 60V) 523 (M$^+$+1).

EXAMPLE 2

N-Acetyl-D-thioproline-4-[(3,5-dichloroisonicotinoyl)amino]-Z-didehydroghenylalanine Lithium hydroxide monohydrate (35 mg, 0.844 mmol) was added to a solution of the compound of Example 1 (368 mg, 0.704 mmol) in a mixture of dioxane (10 ml) and water (10 ml). The mixture was stirred at room temperature for 48 h. Dioxane was removed under reduced pressure and the aqueous residue acidified with glacial acetic acid. The precipitate produced was filtered off then freeze-dried from a mixture of methanol and water to give the title compound as a white fluffy solid (220 mg, 61%). δH (DMSO-d$^6$, 390K) 10.6 (1H, br s, pyCONH), 8.70 (2H, s, PyH), 7.64 (4H, s, ArH), 7.34 (1H, s, C=CH), 4.99 (1H, dd, J 7.3, 4.0 Hz, CHαthiopro), 4.81 (1H, d, J 9.1 Hz, NC$\underline{H}_A$H$_B$S), 4.53 (1H, d, J 9.1 Hz, NCH$_A$$\underline{H}_B$S), 3.40 (1H, dd, J 11.6, 7.4 Hz, CHC$\underline{H}_A$H$_B$S), 3.27 (1H, dd, J 11.6, 4.0 Hz, CHCH$_A$$\underline{H}_B$S) and 2.11 (3H, s, COCH$_3$) (acid proton and CHCON$\underline{H}$ not observed); m/z (ESI, 60V) 509 (M$^+$+1).

EXAMPLE 3

N-Acetyl-D-thioproline-4-[(3,5-dichloroisonicotinoyl)amino]-E-didehydronhenylalanine Methyl Ester A solution of Intermediate 1 (708 mg, 2 mmol) in THF (10 ml) was added to a solution of LDA (2M solution, Aldrich, 1 ml, 2 mmol) in THF (5 ml) at −78°. The suspension was warmed to 0° and a solution of Intermediate 2 (590 mg, 2 mmol) in THF (5 ml) was added followed by DMF (2 ml) to dissolve the precipitate. The mixture was stirred at room temperature ovenight. The solvents were removed under reduced pressure. The residue was dissolved in EtOAc (200 ml), washed with water (2×50 ml) and brine (50 ml), dried (Na$_2$SO$_4$) and evaporated under reduced pressure. The crude product contained a mixture of double bond geometric isomers: E/Z, ~35/65 determined by NMR. Column chromatography (SiO$_2$; EtOAc/MeOH, 97:3) gave some of the less polar E isomer—the title compound (125 mg) as a white solid. δH (DMSO-d$^6$, 390K) 10.56 (1H, s, pyCONH), 9.55 (1H, s, CHCON$\underline{H}$), 8.71 (2H, s, pyH), 7.61 (2H, br d, J 7.9 Hz, ArH), 7.30 (2H, d, J 8.5 Hz, ArH), 6.86 (1H, s, C=CH), 4.94 (1H, dd, J 7.3, 3.9 Hz, CHαthiopro), 4.80 (1H, d, J 9.1 Hz, NC$\underline{H}_A$H$_B$S), 4.53 (1H, d, 19.1 Hz, NCH$_A$$\underline{H}_B$S), 3.67 (3H, s, CO$_2$Me), 3.39 (1H, dd, J 11.6, 7.3 Hz, CHC$\underline{H}_A$H$_B$S), 3.32 (1H, dd, J 11.6, 3.9 Hz, CHCH$_A$$\underline{H}_B$S) and 2.10 (3H, s, COCH$_3$); m/z (ESI, 60V) 523 (M$^+$+1).

EXAMPLE 4

N-Acetyl-D-thioproline-4-[(3,5-dichloroisonicotinoyl)amino]-E-didehydrophenylalanine Lithium hydroxide monohydrate (11 mg, 0.25 mmol) was added to a solution of the compound of Example 3 (110 mg, 0.21 mmol) in a mixture of dioxane (5 ml) and water (5 ml). The mixture was stirred at room temperature for 24 h. The dioxane was removed under reduced pressure. The aqueous residue was acidified with glacial acetic acid. The precipitate formed was filtered off and freeze-dried from a mixture of methanol and water to give the title compound as a pale yellow solid (56 mg, 52%). δH (DMSO-d$^6$, 390K) 10.53 (1H, s, pyCONH), 9.33 (1H, s, CHCON$\underline{H}$), 8.70 (2H, s, pyH), 7.58 (2H, br d, J 7.7 Hz, ArH), 7.37 (2H, d, J 8.5 Hz, ArH), 6.99 (1H, s, C=CH), 4.96 (1H, dd, J 7.3, 3.9 Hz, CHαthiopro), 4.81 (1H, d, J 9.1 Hz, NC$\underline{H}_A$H$_B$S), 4.53 (1H, d, J 9.1 Hz, NCH$_A$$\underline{H}_B$S), 3.39 (1H, dd, J 11.6, 7.3 Hz, CHC$\underline{H}_A$H$_B$S), 3.24 (1H, dd, J 11.6, 3.9 Hz, CHCH$_A$$\underline{H}_B$S) and 2.10 (3H, s, COCH$_3$) (acid proton not observed); m/z (ESI, 60V) 509 (M$^+$+1). The geometry of the double bond was confirmed as E by observation of an n.O.e. between the olefinic proton and the NH of the central amide bond. No n.O.e was seen between the corresponding protons in the Z double bond compound.

EXAMPLE 5

N-Trimethylacetyl-4-[(3,5-dichloroisonicotinoyl)amino]-Z-didehydrophenylalanine Methyl Ester DBU (22 μl, 1.5 mmol) was added to a solution of Intermediate 3 (422 mg, 1.5 mmol) and Intermediate 2 (443 mg, 1.5 mmol) in CH$_2$Cl$_2$ (15 ml). The mixture was stirred at room temperature overnight, diluted with CH$_2$Cl$_2$ (20 ml), washed with dilute hydrochloric acid (1M, 30 ml), dried (Na$_2$SO$_4$) and evaporated under reduced pressure. The solid obtained was re-suspended in CH$_2$Cl$_2$ (~10 ml) and filtered off to give the title compound as a white solid (356 mg, 53%). δH (DMSO-d$^6$) 11.09 (1H, s, ArCONH), 9.09 (1H, s, t-BuCON$\underline{H}$), 8.81 (2H, s, pyH), 7.67 (4H, s, ArH), 7.26 (1H, s, C=CH), 3.70 (3H, s, CO$_2$Me) and 1.21 (9H, s, t-Bu); m/z (ESI, 60V) 450 (M$^+$+1).

EXAMPLE 6

N-Trimethylacetyl-4-[(3,5-dichloroisonicotinoyl) amino]-Z-didehydrophanylalanine Lithium hydroxide monohydrate (65 mg, 1.56 mmol) was added to the compound of Example 5 (350 mg, 0.778 mmol)

in a mixture of dioxane (8 ml) and water (8 ml). The solution was stirred at room temperature overnight. The dioxane was removed under reduced pressure and the acqueous residue acidified (1M hydrochloric acid, pH1). The precipitate formed was filtered off, washed with water and dried to give the title compound as a white solid (300 mg, 88%). $\delta$H (DMSO-$d^6$) 12.49 (1H, br s, $CO_2$H), 11.07 (1H, s, ArCONH), 8.93 (1H, s, t-BuCONH), 8.81 (2H, s, pyH), 7.67 (2H, d, J 9.1 Hz, ArH), 7.63 (2H, d, J 9.1 Hz, ArH), 7.28 (1H, s, C=CH) and 1.20 (9H, s, t-Bu); m/z (ESI, 60V) 436 ($M^+$+1).

EXAMPLE 7

N-Trimethylacetyl-4-[(3,5-dichloroisonicotinoyl)amino]-E-didehydrophenylalanine Methyl Ester A solution of Intermediate 3 (562 mg, 2 mmol) in THF (10 ml) was added to a solution of LDA (2M solution, Aldrich, 1.0 ml, 2 mmol) in THF (5 ml) at −78°. The solution was warmed slowly to 0° and a solution of Intermediate 2 (590 mg, 2 mmol) in THF (5 ml) was added. The mixture was stirred at room temperature overnight. Water (50 ml) was added and the mixture extracted with $CH_2Cl$ (2×150 ml). The combined extracts were dried ($Na_2SO_4$) and evaporated under reduced pressure. The crude product contained a mixture of double bond geometric isomers, E/Z ~40/60 determined by NMR. Column chromatography ($SiO_2$; $CH_2Cl_2$/MeOH, 95:5) followed by chromatotron separation ($SiO_2$; EtOAc/hexane, 50/50) gave some of the less polar, E isomer, the title compound (130 mg). $\delta$H (DMSO-$d^6$) 10.98 (1H, s, ArCONH), 9.52 (1H, s, t-BuCONH), 8.80 (2H, s, pyH), 7.62 (2H, d, J 8.6 Hz, ArH), 7.22 (2H, d, J 8.6 Hz, ArH), 6.56 (1H, s, C=CH), 3.62 (3H, s, $CO_2$Me) and 1.16 (9H, s, t-Bu); m/z (ESI, 60V) 450 ($M^+$+1)

EXAMPLE 8

N-Trimethylacetyl-4-[(3,5-dichloroisonicotinoyl)amino]-E-didehydrophenylalanine Lithium hydroxide monohydrate (22 mg, 0.533 mmol) was added to the compound of Example 7 (120 mg, 0.26 mmol) in a mixture of dioxane (5 ml) and water (5 ml). The solution was stirred at room temperature overnight. The dioxane was removed under reduced pressure and the aqueous residue acidified (1M hydrochloric acid). The precipitate formed was filtered off, washed with water and dried to give the title compound as a white solid (87 mg). $\delta$H (DMSO-$d^6$) 12.67 (1H, br s, $CO_2$H), 10.96 (1H, s, ArCONH), 9.33 (1H, s, t-BuCONH), 8.80 (2H, s, pyH), 7.59 (2H, d, J 8.7 Hz, ArH), 7.32 (2H, d, 18.7 Hz, ArH), 6.55 (1H, s, C=CH) and 1.17 (9H, s, t-Bu); m/z (ESI, 60V) 436 ($M^+$+1).

EXAMPLE 9

N-(2-Chloronicotinoyl)-4-[(3,5-dichloroisonicotinoyl)amino]-Z-didehydrophenylalanine Methyl Ester DBU (22$\mu$l, 1.5 mmol) was added to a solution of Intermediate 4 (508 mg, 1.5 mmol) and Intermediate 2 (443 mg, 1.5 mmol) in $CH_2Cl_2$ (15 ml). The mixture was stirred at room temperature overnight, diluted with $CH_2Cl_2$ (200 ml), washed with dilute hydrochloric acid (50 ml), dried ($Na_2SO_4$) and evaporated under reduced pressure. Column chromatography ($SiO_2$, $CH_2Cl_2$/MeOH; 95:5 to 90:10) gave the product as a yellow viscous oil. Crystallisation from MeOH gave the title compound (418 mg) as small off-white crystals m.p. 223–224°. $\delta$H (DMSO-$d^6$) 11.13 (1H, br s, ArCONHAr), 10.32 (1H, br s, pyCONHC=C), 8.81 (2H, s, pyH), 8.54 (1H, dd, J 4.8, 1.8 Hz, pyH), 8.01 (1H, dd, J 7.5, 1.9 Hz, pyH), 7.79 (2H, d, J 8.8 Hz, ArH), 7.72 (2H, d, J 8.8 Hz, ArH), 7.59 (1H, dd, J 7.5, 4.8 Hz, pyH), 7.43 (1H, s, C=CH) and 3.79 (3H, s, $CO_2$Me); m/z (ESI, 60V) 505 ($M^+$+1).

EXAMPLE 10 a) N-(2-Chloronicotinoyl)-4-[(3,5-dichloroisonicotinoyl)amino]-Z-didehydrophenylalanine Lithium hydroxide monohydrate (68 mg, 1.61 mmol) was added to the compound of Example 9 (407 mg, 0.805 mmol) in a mixture of dioxane (8 ml) and water (8 ml). The reaction mixture was stirred at room temperature for 24 h. The dioxane was evaporated under reduced pressure. The aqueous residue was acidified (dilute hydrochloric acid) and the precipitate formed filtered off, washed with water and dried to giver the title compound as an off-white solid (354 mg, 89%). $\delta$H (DMSO-$d^6$) 11.14 (1H, br s, $CO_2$H), 11.11 (1H, s, pyCONHAr), 10.16 (1H, s, pyCONHC=C), 8.81 (2H, s, pyH), 8.53 (1H, dd, J 4.8, 1.8 Hz, pyH), 7.97 (1H, dd, J 7.5, 1.8 Hz, pyH), 7.77 (2H, d, J 8.8 Hz, ArH), 7.71 (2H, d, J 8.8 Hz, ArH), 7.58 (1H, dd, J 7.5, 4.8 Hz, pyH) and 7.44 (1H, s, C=CH); m/z (ESI, 60V) 491 ($M^+$+1).

The following compounds of Examples 10b) and 10c) were prepared in a similar manner by hydrolysis of the corresponding methyl ester:

b) (Z)-3-{4-[3,5-Dichloro-4-pyridinyl)methoxy]phenyl}-2-[(2,6-dimethoxybenzoyl)amino]-2-propenoic Acid Prepared as an off-white solid: $\delta_H$ (DMSO-$d^6$), 12.4 (1H, br s), 9.53 (1H, s), 8.73 (2H, s), 7.83 (2H, d, J 8.8 Hz), 7.32 (1H, t, J 8.3 Hz), 7.25 (1H, s), 7.09 (2H, d, J 8.8 Hz), 6.70 (2H, d, J 8.4 Hz), 5.31 (2H, s), 3.79 (6H, s); m/z (ESI) 503 ($MH^+$). The ester starting material was prepared from Intermediate 7 and Intermediate 8 in a similar manner to the compounds of Example 9.

c) (Z)-2-{[(2-Chloro-3-pyridinyl)carbonyl]amino}-3-{4-[(3,5-dichloro-4-pyridinyl)methoxy]phenyl}-2-propenoic Acid Prepared as a pale yellow solid. $\delta_H$ (DMSO-$d^6$), 12.8 (1H, br s), 10.09 (1H, s), 8.73 (2H, s), 8.52 (1H, dd, J 4.9, 1.9 Hz), 7.93 (1H, dd, J 7.6, 1.9 Hz), 7.75 (2H, d, J 8.9 Hz), 7.56 (1H, dd, J 7.6, 4.9 Hz), 7.46 (1H, s), 7.13 (2H, d, J 8.9 Hz), 5.29 (2H, s); m/z (ESI) 480 ($MH^+$). The ester starting material was prepared from Intermediate 4 and Intermediate 7 in a similar manner to the compound of Example 9.

EXAMPLE 11

N-(2-Chloronicotinoyl)-4-[(3,5-chloronicotinoyl)amino]-E-didehydrophenylalanine Methyl Ester A solution of Intermediate 4 (1.83 g, 5 mmol) in THF (15 ml) was added to a solution of LDA (2M, Aldrich, 2.5 ml, 5 mmol) in THF (15 ml) at −78°. The solution was warmed slowly to 0° and a solution of Int ermediate 2(1.48 g, 5 mmol) in THF (15 ml) was added. The reaction mixture was stirred at room temperature overnight. The solvent was evaporated under reduced pressure and the residue dissolved in EtOAc (300 ml), washed with dilute hydrochloric acid (50 ml), water (50 ml) and brine (50 ml), dried ($Na_2SO_4$) and evaporated under reduced pressure. Column chromatography ($SiO_2$; $CH_2Cl_2$/MeOH, 93:7) gave the title compound as a mixture with the corresponding Z isomer (1.80 g). (E:Z~40/60 by NMR). Further purification of a small portion by chromatotron ($SiO_2$; $CH_2Cl_2$/MeOH, 98:2) gave a small sample of the pure title compound free from its Z isomer. δH (DMSO-$d^6$) 11.03 (1H, s, pyCONHAr), 10.74 (1H, s, pyCONHC=C), 8.80 (2H, s, pyH), 8.55 (1H, dd, J4.8, 1.9 Hz, pyH), 8.02 (1H, dd, J 7.5, 1.9 Hz, pyH), 7.65 (2H, d, J 8.6 Hz, ArH), 7.56 (1H, dd, J 7.5, 4.8 Hz, pyH), 7.30 (2H, d, J 8.7 Hz, ArH), 6.70 (1H, s, C=CH) and 4.71 (3H, s, $CO_2Me$); m/z (ESI, 60V) 505 ($M^+$+1).

EXAMPLE 12

N-(2-Chloronicotinoyl)-4-[(3,5-dichloroisonicotinoyl)amino]-E-didehydrophenylalanine Lithium hydroxide monohydrate (161 mg, 3.83 mmol) was added to a solution of the compound of Example 11 [mixture of E+Z isomers E:Z~40:60] (967 mg, 1.91 mmol) in dioxane (15 ml) and water (15 ml). The mixture was stirred at room temperature overnight then refluxed for 30 min. The dioxane was evaporated under reduced pressure. The aqueous residue was acidified (dilute hydrochloric acid) and the precipitate formed filtered off, washed with water and dried to give the title compound as a mixture with the corresponding Z isomer. Purification by preparative HPLC (Waters C18 symmetry column; 1.00 ml/min; MeCN/$H_2O$ 0.1% trifluoroacetic acid) gave a pure sample of the E isomer title compound as a pale yellow powder. δH (DMSO-$d^6$) 13.09 (1H, v br s, $CO_2H$), 11.00 (1H, s, ArCONHAr), 10.54 (1H, s, pyCONHC=C), 8.80 (2H, s, pyH), 8.53 (1H, dd, J, 4.8, 1.9 Hz, pyH), 8.00 (1H, dd, J 7.5, 1.9 Hz, pyH), 7.63 (2H, d, J 8.6 Hz, ArH), 7.56 (1H, dd, J 7.5, 4.8 Hz, ArH), 7.37 (2H, d, J 8.7 Hz, ArH) and 6.73 (1H, s, C=CH); m/z (ESI, 60V) 491 ($M^+$+1).

EXAMPLE 13

Methyl 3-bromo-2-{[(2-chloro-3-pyridinyl)carbonyl]amino}-3-{4-[(3,5-dichloroisonicotinoyl)amino]phenyl}-2-propenoate A suspension of the compound of Example 9 (1.258 g, 2.49 mmol) and N-bromosuccinimide (487 mg, 2.74 mmol) in $CH_2Cl_2$ (25 ml) was stirred in the dark overnight at room temperature. Triethylamine (693 μl, 4.98 mmol) was added and the solution stirred for a further 4 h. The mixture was diluted with $CH_2Cl_2$ (300 ml) and washed with dilute HCl, sodium carbonate solution and sodium thiosulphate solution, dried ($Na_2SO_4$) and concentrated in vacuo. The NMR spectrum of the crude reaction mixture showed the presence of both E and Z isomers (ratio~60:40). Chromatography ($SiO_2$; $CH_2Cl_2$/MeOH, 93:7) followed by crystallisation from EtOAc gave the less polar isomer (Isomer A) of the title compound (298 mg). The crude liquors were concentrated in vacuo and crystallisation from EtOAc/hexane gave the more polar isomer (Isomer B) of the title compound (204 mg).
ISOMER A
$δ_H$ (DMSO-$d^6$), 11.12 (1H, br s, CONH), 10.65 (1H, br s, CONH), 8.81 (2H, s, $Cl_2PyH$), 8.55 (1H,dd, J 4.8, 1.9 Hz, PyH), 7.96 (1H, dd, J 7.6, 1.9 Hz, PyH), 7.71 (2H, d, J 8.7 Hz, ArH), 7.57 (1H, dd, J 7.5, 4.8 Hz, PyH), 7.39 (2H, d, J 8.6 Hz, ArH) and 3.55 (3H, s, $CO_2Me$); m/z (ESI) 585 ($MH^+$).

ISOMER B
$δ_H$ (DMSO-$d^6$), 11.14 (1H, br s, CONH), 10.45 (1H, v br s, CONH), 8.80 (2H, s, $Cl_2PyH$), 8.48 (1H, dd, J 4.8, 1.9 Hz, PyH), 7.82 (1H, dd, J 7.6, 1.9 Hz, PyH), 7.73 (2, d, J 8.4 Hz, ArH), 7.53 (2H, d, J 8.4 Hz, ArH), 7.50 (1H, dd, J 7.6, 4.9 Hz, PyH) and 3.80 (3H, s,$CO_2Me$); m/z (ESI) 585 ($MH^+$).

EXAMPLE 14

Methyl 2-{[(2-chloro-3-pyridinyl)carbonyl]amino}-3-{4-[(3,5-dichloroisonicotinoyl)amino]phenyl}-3-phenylacrylate Tetrakis(triphenylphosphine)palladium (O) (10 mol %, 58 mg) was added to a mixture of the compound of Example 13, Isomer A (288 mg, 0.493 mmol) and phenyl boronic acid (90 mg, 0.74 mmol) in DME (10 ml) and sodium carbonate (2M, 0.986 mmol, 0.493 ml). The mixture was heated at 80° overnight, dlute with $CH_2Cl_2$ (200 ml), washed with diluted HCl and sodium hydrogen carbonate solution, dried ($Na_2SO_4$) and evaporated in vacuo. Chromatography ($SiO_2$; $CH_2Cl_2$/MeOH, 93:7) gave the title compound as a white solid (133 mg). $δ_H$ (DMSO-$d^6$), 11.04 (1H, s, CONH), 10.40 (1H, s, CONH), 8.79 (2H, s, $Cl_2PyH$), 8.48 (1H, dd, J 4.9, 1.9 Hz, PyH), 7.85 (1H, dd, J 7.5, 1.9 Hz, PyH), 7.66 (2H, d, J 8.7 Hz, ArH), 7.51 (1H, dd, J 7.5, 4.9 Hz, PyH), 7.39–7.35 (3H, m, ArH), 7.23 (2H, d, J 8.7 Hz, ArH), 7.07 (2H, m, ArH) and 3.45 (3H, s, $CO_2Me$); m/z (ESI, 60V) 581 ($MH^+$).

EXAMPLE 15

2-{[(2-Chloro-3-pyridinyl)carbonyl]amino}-3-{4-[(3,5-dichloroisonicotinoyl)amino]phenyl}-3-phenylacrylic Acid Lithium hydroxide monohydrate (18 mg, 0.43 mmol) was added to the compound of Example 14 (125 mg, 0.215 mmol) in a mixture of dioxane (5 ml) and water (5 ml). The mixture was heated at reflux for 2 h. The dioxane was removed in vacuo and the aqueous residue acidified with dilute HCl, the precipitate formed was filtered off, washed with water and dried to give the title compound as a pale yellow solid (96 mg). $δ_H$ (DMSO-$d^6$), 12.53 (1H, br s, $CO_2H$), 11.02 (1H, s, ArCONHAr), 10.24 (1H, s, ArCONHC=C), 8.79 (2H, s PyH), 8.48 (1H, dd, J 4.8, 1.9 Hz, PyH), 7.82 (1H, dd, J 7.5, 1.9 Hz, PyH), 7.65 (2H, d, J 8.7 Hz, ArH), 7.51 (1H, dd, J 7.5, 4.8 Hz, PyH), 7.35–7.34 (3H, m, Ph), 7.21 (2H, d, J 8.6 Hz, ArH) and 7.14–7.11 (2H, m, Ph); m/z (ESI, 60V) 567 ($MH^+$).

EXAMPLE 16

Ethyl (Z)-2-{[(2-chloro-3-pyridinyl)carbonyl]amino}-3-{4-[(3,5-dichloroisonicotinoyl)amino]phenyl}-2-butenoate A solution of 3,5-dichloroisonicotinoyl chloride (123 mg, 0.584 mmol) in $CH_2Cl_2$ (2 ml) was added to Intermediate 6 (210 mg, 0.584 mmol) and NMM (67 μl, 0.613 mmol) in $CH_2Cl_2$ (10 ml) at 0°. The mixture was stirred for 24 h at room temperature, diluted with $CH_2Cl_2$ (100 ml), washed with dilute HCl and sodium hydrogen carbonate solution, dried ($Na_2SO_4$) and evaporated in vacuo. Chromatography ($SiO_2$; $CH_2Cl_2$/MeOH, 93:7) gave the title compound as a yellow glass (286 mg) (contains some E isomer. Z:E~85:15). $δ_H$ (DMSO-$d^6$), 11.01 (1H, s, CONH), 9.89 (1H, s, CONH), 8.80 (2H, s, PyH), 8.45 (1H, dd, J 4.8, 1.9 Hz, yH), 7.71–7.66 (3H, m, ArH+PyH), 7.48 (1H, dd, J 87, 4.8 Hz, PyH), 7.40 (2H, d, 1 8.6 Hz, PyH), 4.21 (2H,q, J 7.1 Hz, CO$_2$CH$_{2CH3}$), 2.31 (3H, s,Me) and 1.26 (3H, t, J 7.1 Hz, CO$_2$CH$_2$CH$_3$).

EXAMPLE 17

(Z)-2-{[(2-Chloro-3-pyridinyl)carbonyl]amino}-3-{4-[(3.5-dichloroisonicotinoyl)amino]phenyl}-2-butenoic Acid Lithium hydroxide monohydrate (4.4 mg, 1.05 mml) was added to the compound of Example 16 (280 mg, 0.525 mmol) in a mixture of dioxane (10 ml) and water (10 ml). The mixture was heated at reflux for 2 h. The dioxane was removed in vacuo, the aqueous residue acidified with dilute HCl, the precipitate formed filtered off, washed with water and dried to give a brown solid. Trituration with hot methanol gave the title compound as a pale brown solid (94 mg). $\delta_H$ (DMSO-d$^6$), 12.75 (1H,v br s,CO$_2$H), 10.99 (1H, s, CONH), 9.75 (1H, s, CONH), 8.79 (2H, s, PyH), 8.44 (1H, dd, 14.8, 1.9 Hz, PyH), 7.68–7.64 (3H, m, ArH+PyH), 7.46 (1H, dd, J 7.5, 4.8 Hz, PyH), 7.38 (2H, d, J 8.6 Hz, ArH) and 2.33 (3H, s, Me); m/z (ESI, 70V) 505 (MH$^+$).

The following assays can be used to demonstrate the potency and selectivity of the compounds according to the invention. In each of these assays an IC$_{50}$ value was determined for each test compound and represents the concentration of compound necessary to achieve 50% inhibition of cell adhesion where 100%=adhesion assessed in the absence of the test compound and 0%=absorbance in wells that did not receive cells.

$\alpha_4\beta_1$ Integrin-dependent Jurkat Cell Adhesion to VCAM-Ig 96 well NUNC plates were coated with F(ab)$_2$ fragment goat anti-human IgG Fc$\gamma$-specific antibody [Jackson Immuno Research 109-006-098: 100 $\mu$l at 2 $\mu$g/ml in 0.1M NaHCO$_3$, pH 8.4], overnight at 4°. The plates were washed (3×) in phosphate-buffered saline (PBS) and then blocked for 1 h in PBS/1% BSA at room temperature on a rocking platform. After washing (3× in PBS) 9 ng/ml of purified 2d VCAM-Ig diluted in PBS/1% BSA was added and the plates left for 60 minutes at room temperature on a rocking platform. The plates were washed (3× in PBS) and the assay then performed at 37° for 30 min in a total volume of 200 $\mu$l containing 2.5×10$^5$ Jurkat cells in the presence or absence of titrated test compounds.

Each plate was washed (2×) with medium and the adherent cells were fixed with 100 $\mu$l methanol for 10 minutes followed by another wash. 100 $\mu$l 0.25% Rose Bengal (Sigma R4507) in PBS was added for 5 minutes at room temperature and the plates washed (3×) in PBS. 100 $\mu$l 50% (v/v) ethanol in PBS was added and the plates left for 60 min after which the absorbance (570 nm) was measured.

$\alpha_4\beta_7$ Integrin-dependent JY Cell Adhesion to MAdCAM-Iq

This assay was performed in the same manner as the $\alpha_4\beta_1$ assay except that MAdCAM-Ig (150 ng/ml) was used in place of 2d VCAM-Ig and a sub-line of the $\beta$-lympho blastoid cell-line JY was used in place of Jurkat cells. The IC$_{50}$ value for each test compound was determined as described in the $\alpha_4\beta_1$ integrin assay.

$\alpha_5\beta_1$ Integrin-dependent K562 Cell Adhesion to Fibronectin 96 well tissue culture plates were coated with human plasma fibronectin (Sigma F0895) at 5 $\mu$g/ml in phosphate-buffered saline (PBS) for 2 hr at 37° C. The plates were washed (3× in PBS) and then blocked for 1 h in 100 $\mu$l PBS/1% BSA at room temperature on a rocking platform. The blocked plates were washed (3× in PBS) and the assay then performed at 37° C. in a total volume of 200 $\mu$l containing 2.5×10$^5$ K562 cells, phorbol-12-myristate-13-acetate at 10 ng/ml, and in the presence or absence of titrated test compounds. Incubation time was 30 minutes. Each plate was fixed and stained as described in the $\alpha_4\beta_1$ assay above.

$\alpha_m\beta_2$-Dependent Human Polymorphonuclear Neutrophils Adhesion to Plastic 96 well tissue culture plates were coated with RPMI 1640/10% FCS for 2 h at 37° C. 2×10$^5$ freshly isolated human venous polymorphonuclear neutrophils (PMN) were added to the wells in a total volume of 200 $\mu$l in the presence of 10 ng/ml phorbol-12-myristate-13-acetate, and in the presence or absence of test compounds, and incubated for 20 min at 37° C. followed by 30 min at room temperature. The plates were washed in medium and 100 $\mu$l 0.1% (w/v) HMB (hexadecyl trimethyl ammonium bromide, Sigma H5882) in 0.05M potassium phosphate buffer, pH 6.0 added to each well. The plates were then left on a rocker at room temperature for 60 min. Endogenous peroxidase activity was then assessed using tetramethyl benzidine (TMB) as follows: PMN lysate samples mixed with 0.22% H$_2$O$_2$ (Sigma) and 50 $\mu$g/ml TMB (Boehringer Mannheim) in 0.1M sodium acetate/citrate buffer, pH 6.0 and absorbance measured at 630 nm.

$\alpha$IIb/$\beta_3$-Dependent Human Platelet Aggregation

Human platelet aggregation was assessed using impedance aggregation on the Chronolog Whole Blood Lumiaggregometer. Human platelet-rich plasma (PRP) was obtained by spinning fresh human venous blood anticoagulated with 0.38% (v/v) tri-sodium citrate at 220×g for 10 min and diluted to a cell density of 6×10$^8$/ml in autologous plasma. Cuvettes contained equal volumes of PRP and filtered Tyrode's buffer (g/liter: NaCl 8.0; MgCl$_2$.H$_2$O 0.427; CaCl$_2$ 0.2; KCl 0.2; D-glucose 1.0; NaHCO$_3$ 1.0; NaHPO$_4$.2H$_2$O 0.065). Aggregation was monitored following addition of 2.5 $\mu$M ADP (Sigma) in the presence or absence of inhibitors.

In the above assays the preferred compounds of the invention generally have IC$_{50}$ values in the $\alpha_4\beta_1$ and $\alpha_4\beta_7$ assays of 1 $\mu$M and below. In the other assays featuring a integrins of other subgroups the same compounds had IC$_{50}$ values of 50 $\mu$M and above thus demonstrating the potency and selectivity of their action against $\alpha_4$ integrins.

What is claimed is:

1. A compound of formula (1)

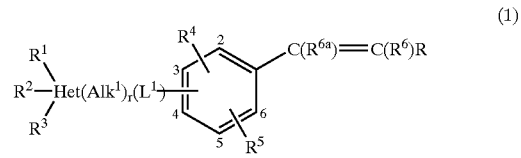

wherein:

Het is a heteroaromatic group;

R$^1$, R$^2$ and R$^3$ which may be the same or different is each a hydrogen or halogen atom, an optionally substituted alkyl, or group —L$^2$(Alk$^2$)$_t$L$^3$(R$^7$)$_u$ in which L$^2$ and L$^3$ which may be the same or different is each a covalent bond or a group selected from the group consisting of —O— or —S— atoms or —C(O)—, —C(O)O—, —C(S)—, —S(O)—, —S(O)$_2$, —N(R$^{12}$)— (where R$^{12}$ is a hydrogen atom or an optionally substituted alkyl group), —CON(R$^{12}$)—, —OC(O)N(R$^{12}$)—, —CSN(R$^{12}$)—, —N(R$^{12}$)CO—, —N(R$^{12}$)C(O)O—, —N(R$^{12}$)CS—, —S(O)$_2$N(R$^{12}$)—, —N(R$^{12}$)S(O)$_2$—, —N(R$^{12}$)CON(R$^{12}$)—, —N(R$^{12}$)CSN(R$^{12}$)—, or —N(R$^{12}$)SO$_2$N(R$^{12}$)—, t is zero or the integer 1, u is an integer 1, 2 or 3, ALK$^2$ is an aliphatic or heteroaliphatic chain and R$^7$ is a hydrogen or halogen atom or a group selected from alkyl, —OR$^8$ (where R$^8$ is a hydrogen atom or an optionally substituted alkyl group), —SR$^8$, NR$^8$R$^9$ (where R$^9$ is a hydrogen atom or an optionally substituted alkyl group), —NO$_2$, —CN, —CO$_2$R$^8$, —OCO$_2$R$^8$, —CONR$^8$R$^9$, —OCONR$^8$R$^9$, —CSNR$^8$R$^9$, —COR$^8$, —OCOR$^8$, —N(R$^8$)COR$^9$, —N(R$^8$)CSR$^9$, —SO$_2$N(R$^8$)(R$^9$), —N(R$^8$)SO$_2$R$^9$, —N(R$^8$)CON(R$^9$)(R$^{10}$), (where R$^{10}$ is a hydrogen atom or an optionally substituted alkyl group) —N(R$^8$)CSN(R$^9$)(R$^{10}$) or —N(R$^8$)SO$_2$N(R$^9$)(R$^{10}$);

Alk$^1$ is an optionally substituted aliphatic or heteroaliphatic chain;

L$^1$ is a covalent bond or a linker atom or group selected from the group consisting of —O— or —S— atoms or —C(O)—, —C(O)O—, —C(S)—, —S(O)—, —S(O)$_2$, —N(R$^{12}$)— (where R$^{12}$ is a hydrogen atom or an optionally substituted alkyl group), —CON(R$^{12}$)—, —OC(O)N(R$^{12}$)—, —CSN(R$^{12}$)—, —N(R$^{12}$)CO—, —N(R$^{12}$)C(O)O—, —N(R$^{12}$)CS—, —S(O)$_2$N(R$^{12}$)—, —N(R$^{12}$)S(O)$_2$—, —N(R$^{12}$)CON(R$^{12}$)—, —N(R$^{12}$)CSN(R$^{12}$)—, or —N(R$^{12}$)SO$_2$N(R$^{12}$)—, wherein L$^1$ is bonded to the 4-position of the phenyl ring to which it is attached and the proviso that (Alk$^1$)$_r$(L$^1$)— is other than a covalent bond;

R$^4$ and R$^5$, which may be the same or different, is each a hydrogen or halogen atom or an alkyl, alkoxy, hydroxy or nitro group;

R$^6$ is a L$^{2a}$R$^{11}$ or L$^{2a}$Alk$^2$R$^{11}$ group (where L$^{2a}$, is —NHCO—, NHCS— or —NHSO$_2$— group);

R$^{6a}$ is an atom or group —L$^2$(Alk$^2$)$_t$L$^3$R$^{11}$ in which L$^2$, L$^3$, Alk$^2$ and t are as previously defined and R$^{11}$ is a hydrogen or halogen atom or an —OR$^8$, —NR$^8$R$^9$, —NO$_2$, —CN, —CO$_2$R$^8$, —CONR$^8$R$^9$, —COR$^8$, —N(R$^8$)COR$^9$, —N(R$^8$)CSR$^9$, —SO$_2$N(R$^8$)(R$^9$), —N(R$^8$)SO$_2$R$^8$, —N(R$^8$)CON(R$^9$)(R$^{10}$), —N(R$^8$)CSN(R$^9$)(R$^{10}$), —N(R$^8$)SO$_2$N(R$^9$)(R$^{10}$) or an optionally substituted aliphatic, heteroaliphatic, cycloaliphatic, heterocycloaliphatic, aromatic or heteroaromatic group;

r is zero or the integer 1;

R is a carboxylic acid (—CO$_2$H) or a derivative thereof; and the salts, solvates, hydrates and N-oxides thereof.

2. A compound according to claim 1 wherein R$^6$ and R$^{6a}$ are in a trans relationship to each other.

3. A compound according to claim 1 wherein R is a —CO$_2$H group.

4. A compound according to claim 1 wherein R$^{6a}$ is a hydrogen atom.

5. A compound according to claim 1 wherein Het is a five- or six-membered monocyclic heteroaromatic group containing one or two heteroatoms selected from oxygen, sulphur or nitrogen atoms.

6. A compound according to claim 5 wherein Het is a pyridyl or pyrimidinyl group.

7. A compound according to claim 1 wherein each of R$^1$, R$^2$ and R$^3$ is a hydrogen atom or an optionally substituted alkyl, —OR$^8$, —SR$^8$, —NR$^8$R$^9$, —COR$^8$, —CO$_2$R$^8$, —NO$_2$, or —CN group.

8. A compound according to claim 1 wherein —(Alk$^1$)$_r$L$^1$— is a —CH$_2$O— or —CON(R$^{12}$)— group.

9. A compound according to claim 1 wherein Alk$^2$ is a C$_{1-4}$alkylene chain.

10. A compound according to claim 1 wherein R$^{11}$ is a hydrogen atom or an optionally substituted cycloaliphatic, heterocycloaliphatic, aromatic or heteroaromatic group.

11. A compound according to claim 10 wherein R$^{11}$ is an optionally substituted C$_{5-7}$cycloaliphatic, C$_{5-7}$heterocycloaliphatic, phenyl or C$_{5-7}$heteroaromatic group.

12. A compound which is:

N-Acetyl-D-thioproline-4-[(3,5-dichloroisonicotinoyl)amino]-Z-didehydrophenylalanine;

N-Acetyl-D-thioproline-4-[(3,5-dichloroisonicotinoyl)amino]-E-didehydrophenylalanine;

N-Trimethylacetyl-4-[(3,5-dichloroisonicotinoyl)amino]-Z-didehydrophenylalanine;

N-Trimethylacetyl-4-[(3,5-dichloroisonicotinoyl)amino]-E-didehydrophenylalanine;

N-(2-Chloronicotinoyl)-4-[(3,5-dichloroisonicotinoyl)amino]-Z-didehydrophenylalanine;

(Z)-3-{4-[(3,5-Dichloro-4-pyridinyl)methoxy]phenyl}-2-[(2,6-dimethoxybenzoyl)amino]-2-propenoic acid;

N-(2-Chloronicotinoyl)-4-[(3,5-dichloroisonicotinoyl)amino]-E-didehydrophenylalanine;

and the salts, solvates, hydrates and N-oxides thereof.

13. A pharmaceutical composition comprising a compound according to claim 1 together with one or more pharmaceutically acceptable carriers, excipients or diluents.

14. A method for the prophylaxis or treatment of a disease or disorder in a mammal in which the extravasation of leukocytes plays a role, comprising administering to a mammal suffering from such a disease or disorder a therapeutically effective amount of a compound according to claim 1.

15. A method according to claim 14 wherein said disease or disorder is selected from the group consisting of inflammatory arthritis, multiple sclerosis, allograft rejection, diabetes, inflammatory dermatoses, asthma, and inflammatory bowel disease.

16. A method according to claim 15 wherein said inflammatory arthritis is selected from the group consisting of rheumatoid arthritis vasculitis and polydermatomyositis.

17. A method according to claim 15 wherein said inflammatory dermatoses are selected from the group consisting of psoriasis and dermatitis.

18. A method for inhibiting, in a mammal, the binding of α4 integrins to the ligands thereof, comprising administering to the mammal an effective amount of a compound according to claim 1.

19. A method according to claim 18 wherein the α4 integrins are α4β1 integrins.

* * * * *

UNITED STATES PATENT AND TRADEMARK OFFICE
CERTIFICATE OF CORRECTION

PATENT NO. : 6,465,471 B1
APPLICATION NO. : 09/346235
DATED : October 15, 2002
INVENTOR(S) : Graham John Warrellow et al.

It is certified that error appears in the above-identified patent and that said Letters Patent is hereby corrected as shown below:

Column 2,
Line 41, before "integrins" change "a" to -- α --.

Column 3,
Line 54, change "$(R^{12})$," to -- $(R^{12})$—, --.

Column 10,
Line 10, change "grop" to -- group --.

Column 11,
Line 13, change "$(L^5)_p(Alk^3)_q R^{15}$" to -- —$(L^5)_p(Alk^3)_q R^{15}$ --.

Column 15,
Line 49, replace "dilsopropyl—" to read -- diisopropyl— --.

Signed and Sealed this

Twentieth Day of June, 2006

JON W. DUDAS
*Director of the United States Patent and Trademark Office*